US008916159B2

(12) United States Patent
Rader et al.

(10) Patent No.: US 8,916,159 B2
(45) Date of Patent: Dec. 23, 2014

(54) SELENOCYSTEINE MEDIATED HYBRID ANTIBODY MOLECULES

(75) Inventors: Christoph Rader, Olney, MD (US); Thomas Hofer, Zurich (CH); Terrence Burke, Jr., Bethesda, MD (US); Joshua Thomas, Frederick, MD (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 482 days.

(21) Appl. No.: 12/570,796

(22) Filed: Sep. 30, 2009

(65) Prior Publication Data

US 2010/0104510 A1    Apr. 29, 2010

Related U.S. Application Data

(63) Continuation-in-part of application No. PCT/US2008/059135, filed on Apr. 2, 2008.

(60) Provisional application No. 60/909,665, filed on Apr. 2, 2007.

(51) Int. Cl.
  *A61K 51/10*   (2006.01)
  *A61K 47/48*   (2006.01)
  *B82Y 5/00*    (2011.01)
  *A61K 39/395*  (2006.01)

(52) U.S. Cl.
  CPC ..... *A61K 47/48753* (2013.01); *A61K 47/48384* (2013.01); *B82Y 5/00* (2013.01); *A61K 47/4863* (2013.01); *A61K 47/48415* (2013.01)
  USPC ..................................................... 424/178.1

(58) Field of Classification Search
  USPC ..................................................... 424/178.1
  See application file for complete search history.

(56) References Cited

U.S. PATENT DOCUMENTS

| 3,832,253 | A  | 8/1974  | DiPalma et al.   |
| 3,854,480 | A  | 12/1974 | Zaffaroni        |
| 4,452,775 | A  | 6/1984  | Kent             |
| 4,667,014 | A  | 5/1987  | Nestor, Jr. et al. |
| 4,748,034 | A  | 5/1988  | de Rham          |
| 5,075,109 | A  | 12/1991 | Tice et al.      |
| 5,239,660 | A  | 8/1993  | Ooi              |
| 5,646,176 | A  | 7/1997  | Golik et al.     |
| 5,736,137 | A  | 4/1998  | Anderson et al.  |
| 6,156,529 | A  | 12/2000 | Willey et al.    |
| 6,303,295 | B1 | 10/2001 | Taylor et al.    |
| 7,141,366 | B1 | 11/2006 | Sandman et al.   |
| 2003/0190676 | A1 | 10/2003 | Barbas et al.  |
| 2004/0198637 | A1 | 10/2004 | Schultz et al. |
| 2008/0254512 | A1 | 10/2008 | Capon          |

FOREIGN PATENT DOCUMENTS

| CA | 2045869      |    | 12/1991 |
| EP | 0835939      | B1 | 11/2005 |
| EP | 1621204      | A1 | 2/2006  |
| WO | WO 94/14787  | A1 | 7/1994  |
| WO | WO 95/21258  | A1 | 8/1995  |
| WO | WO 96/38552  | A1 | 12/1996 |
| WO | WO 00/26358  | A1 | 5/2000  |
| WO | WO 00/31131  | A1 | 6/2000  |
| WO | WO 01/02240  | A1 | 1/2001  |
| WO | WO 01/07081  | A1 | 2/2001  |
| WO | WO 01/12657  | A2 | 2/2001  |
| WO | WO 03/059251 | A2 | 7/2003  |
| WO | WO 2004/003019 | | * 6/2004 |
| WO | WO 2005/118642 | A2 | 12/2005 |
| WO | WO 2006/013003 | A1 | 2/2006  |

OTHER PUBLICATIONS

Rudikoff et al (Proc Natl Acad Sci USA 1982 vol. 79 p. 1979).*
MacCallum et al. (J. Mol. Biol. (1996) 262:732-745).*
De Pascalis et al. The Journal of Immunology (2002) 169, 3076-3084.*
Casset et al. ((2003) BBRC 307, 198-205).*
Vajdos et al. ((2002) J. Mol. Biol. 320, 415-428).*
Holm et al ((2007) Mol. Immunol. 44: 1075-1084).*
Chen et al. J. Mol. Bio. (1999) 293, 865-881.*
Wu et al. (J. Mol. Biol. (1999) 294, 151-162).*
Ward et al. (Nature 341:544-546 (1989)).*
Smith-Gill et al. (J. Immunol. 139:4135-4144 (1987)).*
Kumar et al. (J. Biol. Chem. 275:35129-35136 (2000).*
Song et al. (Biochem Biophys Res Comm 268:390-394 (2000)).*
Brummell et al. (Biochemistry 32:1180-1187 (1993)).*
Kobayashi et al. (Protein Engineering 12:879-844 (1999)).*
Burks et al. (PNAS 94:412-417 (1997)).*
Jang et al. (Molec. Immunol. 35:1207-1217 (1998)).*
Brorson et al. (J. Immunol. 163:6694-6701 (1999)).*
Coleman (Research in Immunol. 145:33-36 (1994)).*
ATTC search output for "rituximab" (p. 1; Jan. 14, 2012).*
ATTC search output for "KYK2.0" (p. 1; Jan. 14, 2012).*
Ibragimova and Eade (Biophysical Journal, Oct. 1999, vol. 77, pp. 2191-2198).*
Lazar et al Molecular and Cellular Biology Mar. 1988 vol. 8 No. 3 1247-1252.*
Schwartz et al, Proc Natl Acad Sci USA vol. 84:6408-6411 (1987).*

(Continued)

*Primary Examiner* — Lynn Bristol
(74) *Attorney, Agent, or Firm* — Leydig, Voit & Mayer, Ltd.

(57) ABSTRACT

The invention provides methods and compositions employing hybrid molecules of a synthetic molecule and antibody or antibody fragment comprising a selenocysteine residue, wherein the synthetic molecule is covalently linked to the antibody or antibody fragment at the selenocysteine residue. The invention also provides a composition comprising a hybrid molecule as described above and a pharmaceutically acceptable carrier. The invention further provides for methods of making the hybrid molecules, and methods of using the hybrid molecule described above to inhibit cell surface receptor binding.

22 Claims, 21 Drawing Sheets

(56) References Cited

OTHER PUBLICATIONS

Lin et al Biochemistry USA vol. 14:1559-1563 (1975).*
Burgess et al, Journal of Cell Biology vol. 111 Nov. 1990 2129-2138.*
Abraham et al., *Proc. Nat. Acad. Sci.*, 104 (13): 5584-5589 (2007).
Baker, *Nature Biotechnology*, 23 (9): 1065-1078 (2005).
Bulinski et al., *J. Cell Sci.*, 110: 3055-3064 (1997).
Chmura et al., *Proc. Nat. Acad. Sci.*, 98 (15): 8480-8484 (2001).
Gastinel, *Proc. Natl. Acad. Sci.*, USA, 89: 638-642 (1992).
Gieselman et al., *ChemBioChem*, 3: 709-716 (2002).
Gieselman et al., *Organic Letters*, 3 (9): 1331-1334 (2001).
Gorlatov et al., *Archives of Biochemistry and Biophysics*, 369 (1): 133-142 (1999).
Gorlatov et al., *Proc. Nat. Acad. Sci*, 95: 8520-8525 (1998).
Hofer et al., *Proc. Nat. Acad. Sci*, 105 (34): 12451-12456 (2008).
Hondal et al., *Journal of the American Chemical Society* (123): 5140-5141 (2001).
Johansson et al., *Nature Methods*, 1 (1), pp. 1-6 (2004).
Kruyukov et al., *Science* (300), pp. 1439-1443 (2003).
Kwong et al. *J. Mol. Biol*, (384): 1143-56 (2008).
Lee et al., *Journal of Biological Chemistry*, 274 (8): 4722-4734 (1999).
Lee et al., *Proc. Nat. Acad. Sci*, 97 (6): 2521-2526 (2000).
Lo et al., *Protein Eng.*, 6: 495-500 (1998).
Luo et al., *Biochem. and Biophys. Research Comm.*, 198 (3): 1240-1247 (1994).
Muhlradt, *Cancer Research*: 3344-3346 (1997).
Nalvarte et al., *J. Biol Chem.*, 279: 54510-54517 (2004).
Nicolaou, *Nature*, 387: 268-272 (1997).
Panda, *J. Biol Chem.*, 271: 29807-29812 (1996).
Panda, *Proc. National Acad. Sci.*, 94: 10560-10564 (1997).
Peng et al., *Nat. Chem Biol.*, 2: 381-389 (2006).
Popkov et al., *Int. J. Cancer*, 119: 1194-1207 (2006).
Quaderer et al., *Helvetica Chimica Acta*, 84:1197-1206 (2001).
Rader et al., *FASEB J.*, 16: 2000-2002 (2002).
Rader et al., *Proc. Nat. Acad. Sci*, 100(9): 5396-5400 (2003).
Reichert et al., *Nature Biotechnology*, 23 (9): 1073-1078 (2005).
Roopenian et al., *Nat Rev Immunol.*, 7: 715-725 (2007).
Service et al., *Science*, 274: 2009 (1996).
Song et al., *Bioorg Med Chem. Lett*, 14: 161-165 (2004).
Spiekermann et al., *J. Exp. Med.*, 196: 303-310 (2002).
Terpe, *Appl. Microbiol. Biotechnol.*, 60: 523-533 (2003).
Thomas et al., *Bioorg Medicinal Chem. Letters*, 18: 5785-88 (2008).
Thomas et al., *Poster MEDI-409*, 238th ACS Nat'l Meeting, Washington, D.C. (2009).
Vasquez, *Mol. Biol Cell*, 8: 973-985 (1997).
Wu et al., *Nature Biotechnology*, 23(9): 1137-1146 (2005).
Zhang et al., *J. Immunol.*, 179: 4910-8 (2007).
Zuckier et al., *Cancer Research*, 58:3905-08 (1998).
Cui et al., *J. Biological Chem.*, 287(34): 28206-28214 (2012).
Hofer et al., *Biochemistry*, 48: 12047-12057 (2009).
Li et al., *Methods*, 65: 133-138 (2014).
Rader, *Trends in Biotechnology*, 32(4): 186-197 (2014).

* cited by examiner

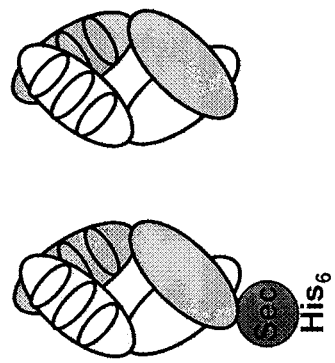
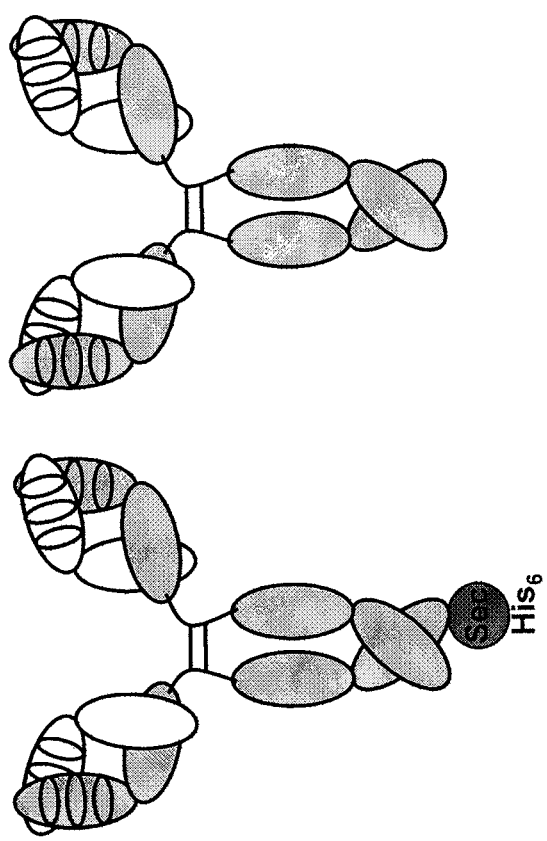
Figure 10A
Figure 10B
Figure 10C

US 8,916,159 B2

SELENOCYSTEINE MEDIATED HYBRID ANTIBODY MOLECULES

CROSS-REFERENCE TO RELATED APPLICATIONS

This patent application is a continuation-in-part of International Patent Application PCT/US08/59135, filed Apr. 2, 2008, which claims the benefit of U.S. Provisional Patent Application No. 60/909,665 filed Apr. 2, 2007, each of which is incorporated herein by reference.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 4203 Byte ANSI (Text) file named "SequenceListing_ST25.TXT," created on Sep. 25, 2009.

BACKGROUND OF THE INVENTION

Existing cancer treatments, such as cytotoxic therapy, can be effective at destroying tumors and other malignant cells. In the process, however, such therapies can also damage healthy cells and tissues. Some of the undesirable side effects associated with cancer treatments such as cytotoxic therapy include anemia, immunosuppression, decreased wound healing, and damage to mucosal tissues. Similar problems exist in conventional treatments for other conditions such as autoimmune or inflammatory disorders as well as infectious diseases. Many of the undesirable side effects associated with treatments for these conditions are caused by interactions between the treatment agent and non-diseased cells.

Targeted drug therapies are increasingly favored for use in treating conditions such as cancer, autoimmune or inflammatory disorders, and infectious diseases. Targeted therapies can act directly on diseased cells with relatively less activity toward non-diseased cells. Therefore, targeted therapies can be administered with a greater efficacy and/or a relatively lower dose than non-targeted therapies.

BRIEF SUMMARY OF THE INVENTION

The invention provides a hybrid molecule of a synthetic molecule and antibody or antibody fragment comprising a selenocysteine residue, wherein the synthetic molecule is covalently linked to the antibody or antibody fragment at the selenocysteine residue, as well as compositions and methods involving same.

In particular, the invention provides a composition comprising such a hybrid molecule and a pharmaceutically acceptable carrier. The invention also provides for methods of using such a hybrid molecule to inhibit cell surface receptor binding. The invention further provides for methods of preparing such a hybrid molecule comprising (i) providing a gene encoding an antibody or an antibody fragment, wherein the gene comprises (a) a UGA codon, and (b) a selenocysteine insertion sequence element; (ii) expressing the gene in a mammalian expression system, in a medium comprising sodium selenite, to produce an antibody or antibody fragment; (iii) purifying the expressed antibody or antibody fragment; and (iv) incubating the antibody or antibody fragment with the small synthetic molecule, a buffer, and a reducing agent to provide a hybrid molecule comprising the small molecule and the antibody or antibody fragment, wherein the small molecule is covalently bound to the antibody or antibody fragment at the selenocysteine residue.

BRIEF DESCRIPTION OF THE SEVERAL VIEWS OF THE DRAWING(S)

FIG. 1A is a schematic representation of an IgG1 antibody molecule containing two identical light chains (white) and two identical heavy chains (gray). The light chain consists of one N terminal variable domain ($V_L$) followed by one constant domain ($C_L$). The heavy chain consists of one N-terminal variable domain ($V_H$) followed by three constant domains ($CH_1$, $CH_2$, and $CH_3$). The antigen binding site exists at the convergence of six complementarity determining regions (CDRs), three provided by each of $V_H$ and $V_L$. F(ab')$_2$ and Fc fragments are also indicated.

FIG. 1B is a schematic representation of a mammalian expression vector based on pCEP4 (Invitrogen, Carlsbad, Calif.) encoding a human Fc protein with a C-terminal selenocysteine. In the presence of 1 µM sodium selenite, approximately 1 mg Fc protein with histidine tag (Fc-Sec-His) was purified from 500 mL supernatant of transiently transfected human embryonic kidney (HEK) 293F cells (20%), while approximately 4 mg Fc without histidine tag (Fc-stop) was purified (80%).

Figures 9A, 9B:
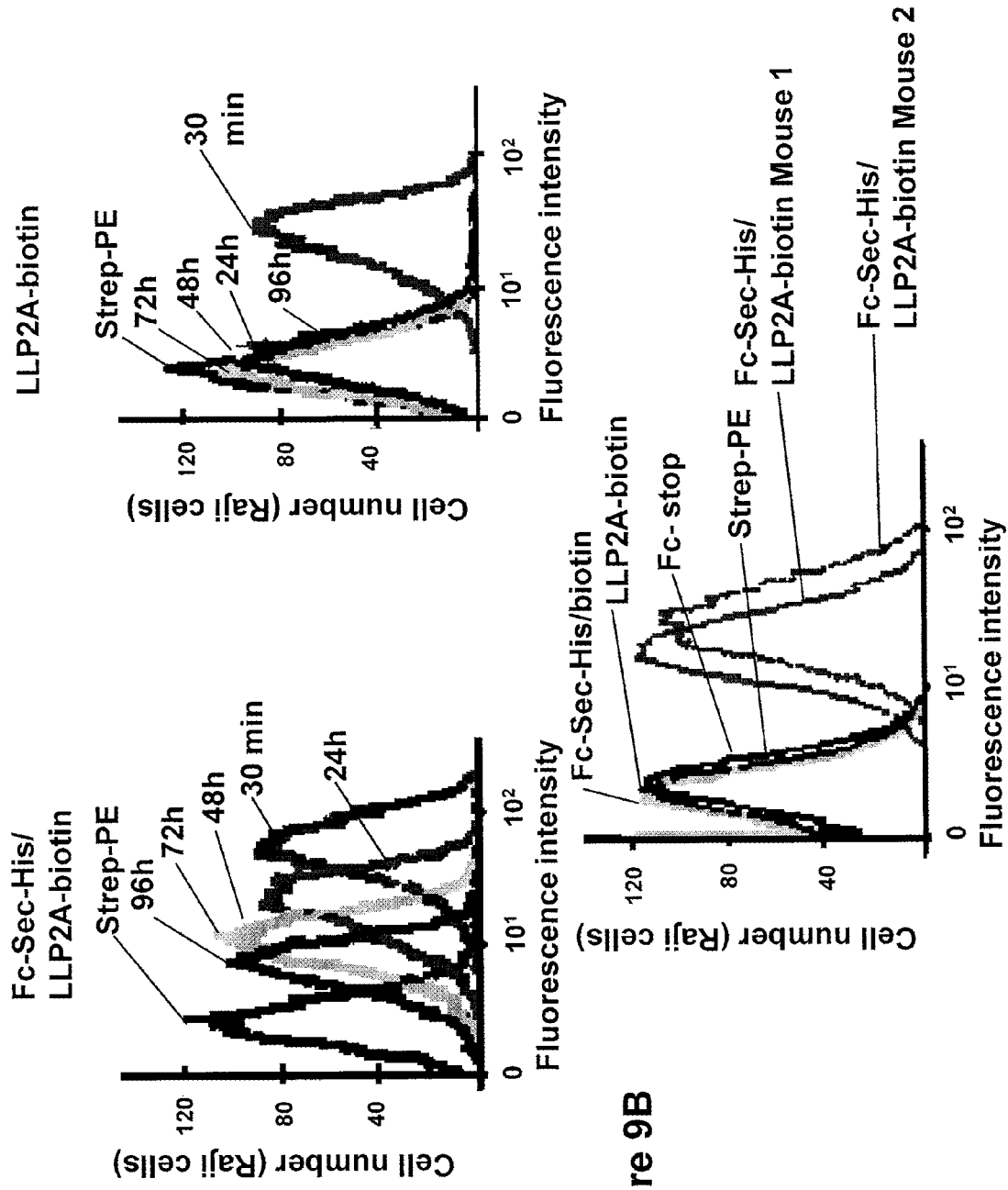
FIG. 9A is a flow cytometry plot comparing the circulatory half-life of Fc-Sec-His/LLP2A-biotin and free LLP2A-biotin in mice at various time points. Typical results based on three individual mice in each treatment group are shown.

FIG. 9B is a flow cytometry plot for comparison of the efficacy of transcytosis following intragastric delivery of Fc-stop, Fc-Sec-His/LLP2A-biotin, and Fc-Sec-His/biotin, as well as an equimolar amount of free LLP2A-biotin to neonatal mice. Typical results based on two individual neonatal mice in each treatment group are shown for Fc-stop, Fc-Sec-His/biotin, and free LLP2A-biotin (all negative). The results of both mice (solid and dotted line) are shown for Fc-Sec-His/LLP2A-biotin.

FIG. 10A is a schematic overview of the engineered immunoglobulin (Ig) proteins Rituximab-Sec-His light and heavy chains in a bi-directional vector.

FIG. 10B is a schematic overview of Rituximab-Sec-His.

FIG. 10C is a schematic overview of Rituxi-Fab-Sec-His.

Figure 11A:
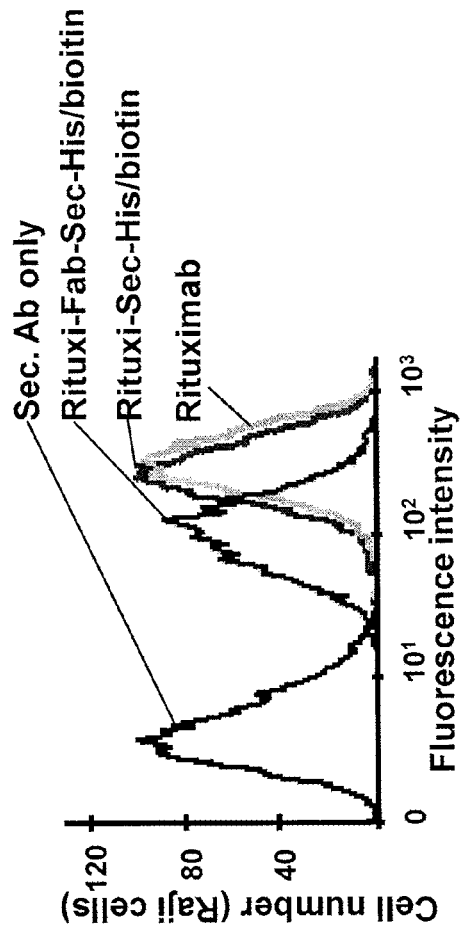

FIG. 11A is a flow cytometry plot of Rituximab-Sec-His/biotin, Rituxi-Fab-Sec-His/biotin, and Rituximab, incubated with Raji cells and stained with PE coupled goat anti-human Fab polyclonal antibodies.

Figure 11B:
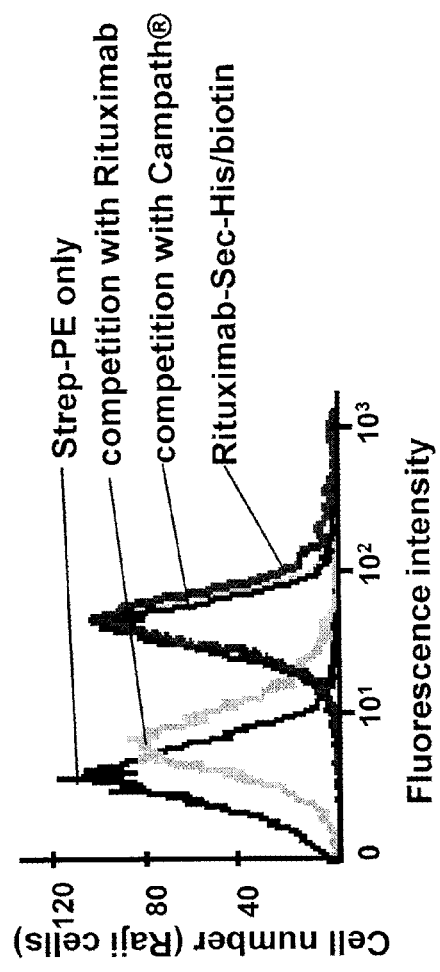

FIG. 11B is a flow cytometry plot of the specific binding of Rituximab-Sec-His/biotin as compared with Rituximab.

Figure 11C:
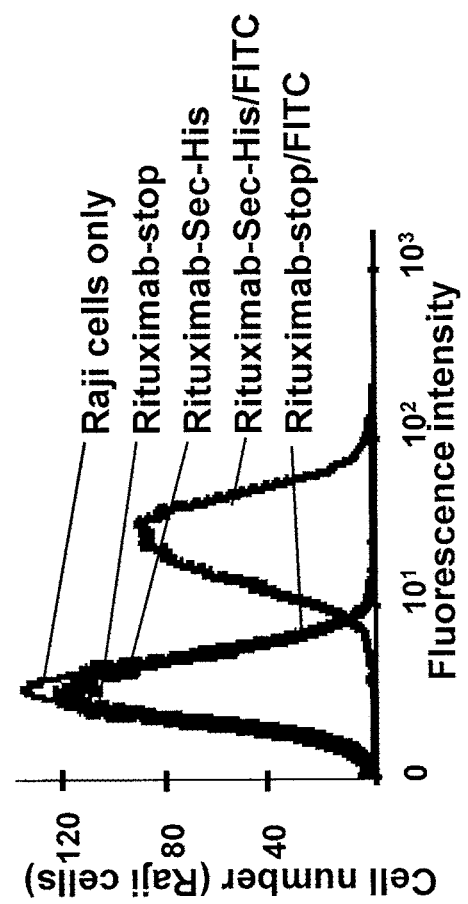

FIG. 11C is a flow cytometry plot of Rituximab-Sec-His and Rituximab-stop, upon exposure to a FITC derivative with an electrophilic maleimide moiety followed by incubation with Raji cells.

Figure 12B:
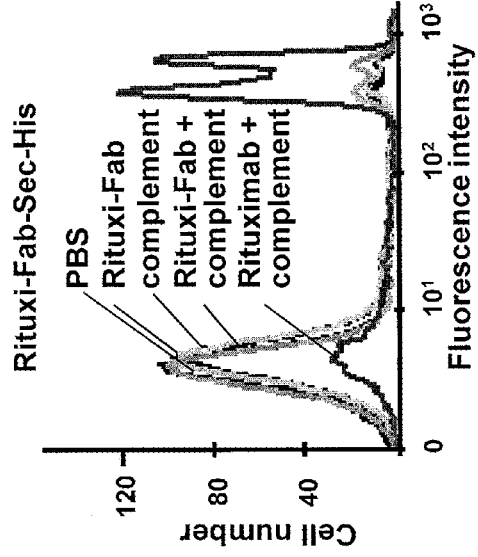
Figure 12D:
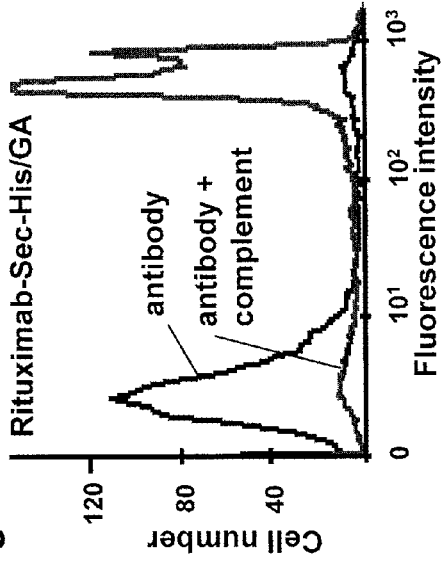
Figure 12A:
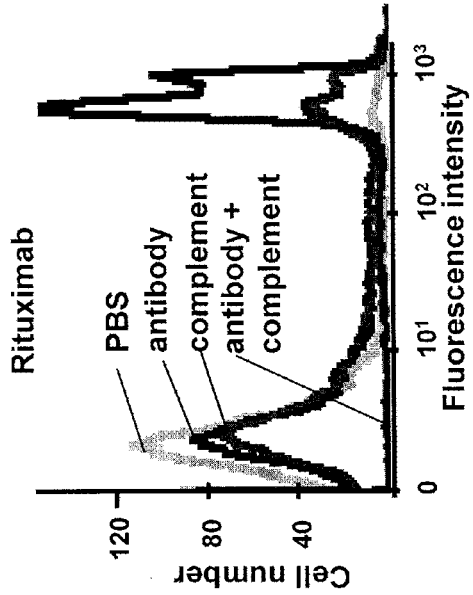

FIG. 12A is a flow cytometry plot of Rituximab, rabbit serum, Rituximab in combination with rabbit serum, and a negative control, using propium iodide staining as a marker of dead/dying cells.

FIG. 12B is a flow cytometry plot of Rituxi-Fab-Sec-His, rabbit serum, Rituxi-Fab-Sec-His in combination with rabbit serum, and a negative control, using propium iodide staining as a marker of dead/dying cells.

Figure 12C:
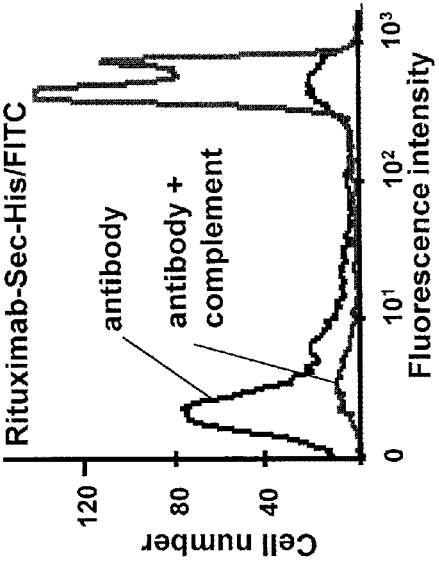

FIG. 12C is a flow cytometry plot of Rituximab-Sec-His/FITC, alone and in combination with rabbit serum.

FIG. 12D is a flow cytometry plot of Rituximab-Sec-His/Geldanamycin, alone and in combination with rabbit serum.

Figure 13:
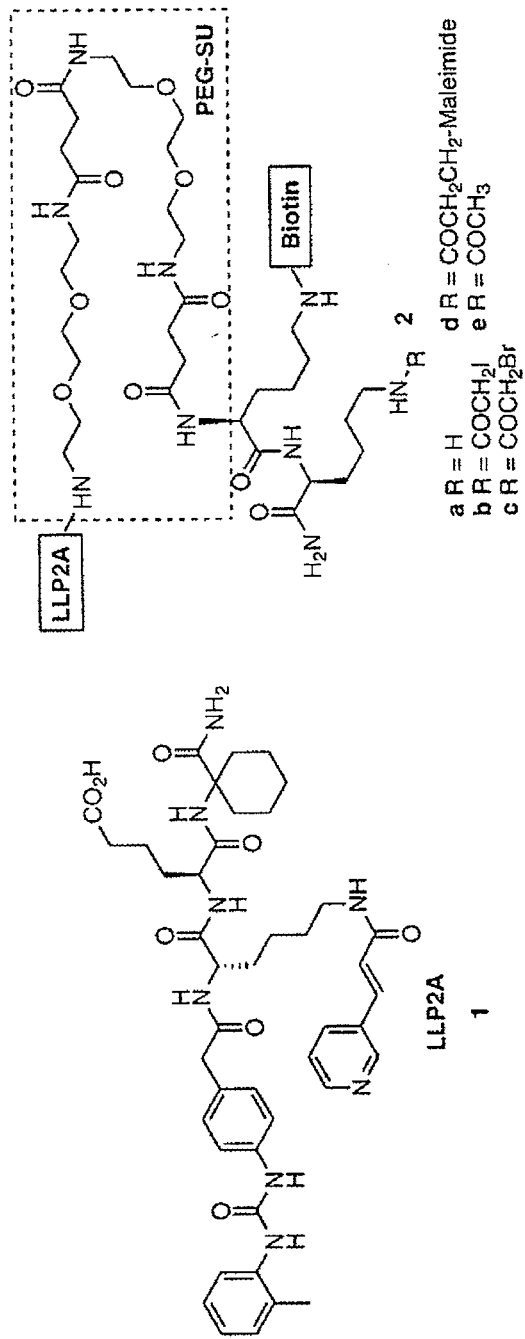

FIG. 13 depicts the chemical structure of the PEG-SU-Lys-Lys-mal trifunctional linker, showing sites of attachment for bitoin and LLP2A, with R showing the intended site of Fc-Sec attachment.

Figure 14:
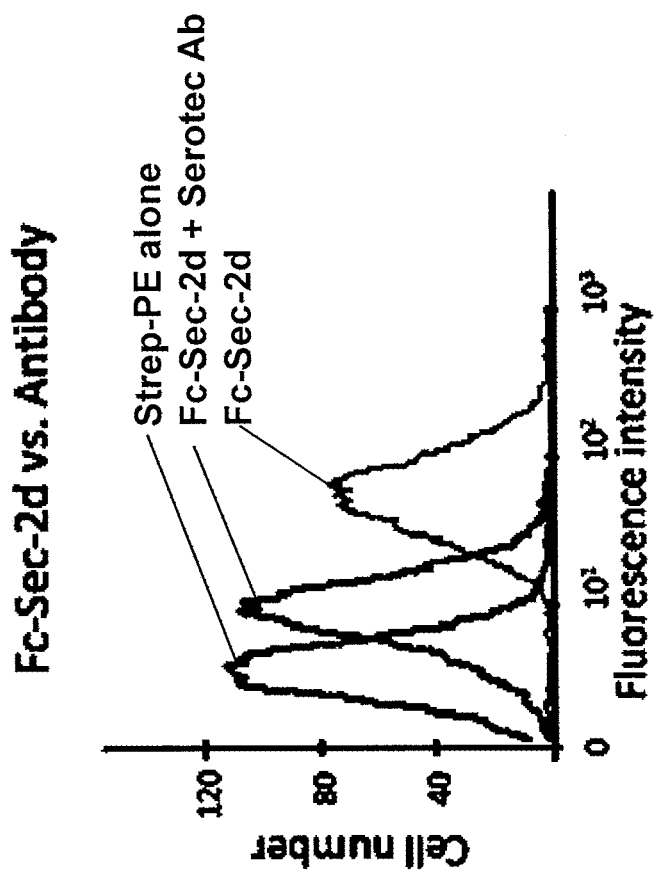

FIG. 14 is a flow cytometry plot of Fc-Sec-LLP2A, coupled using the PEG-SU-Lys-Lys-mal trifunctional linker, alone and in combination with a monoclonal mouse anti-human integrin $\alpha_4$ antibody. Streptavidin coupled phycoerythrin (Strep-PE) was used for detection and as a negative control.

Figure 15:
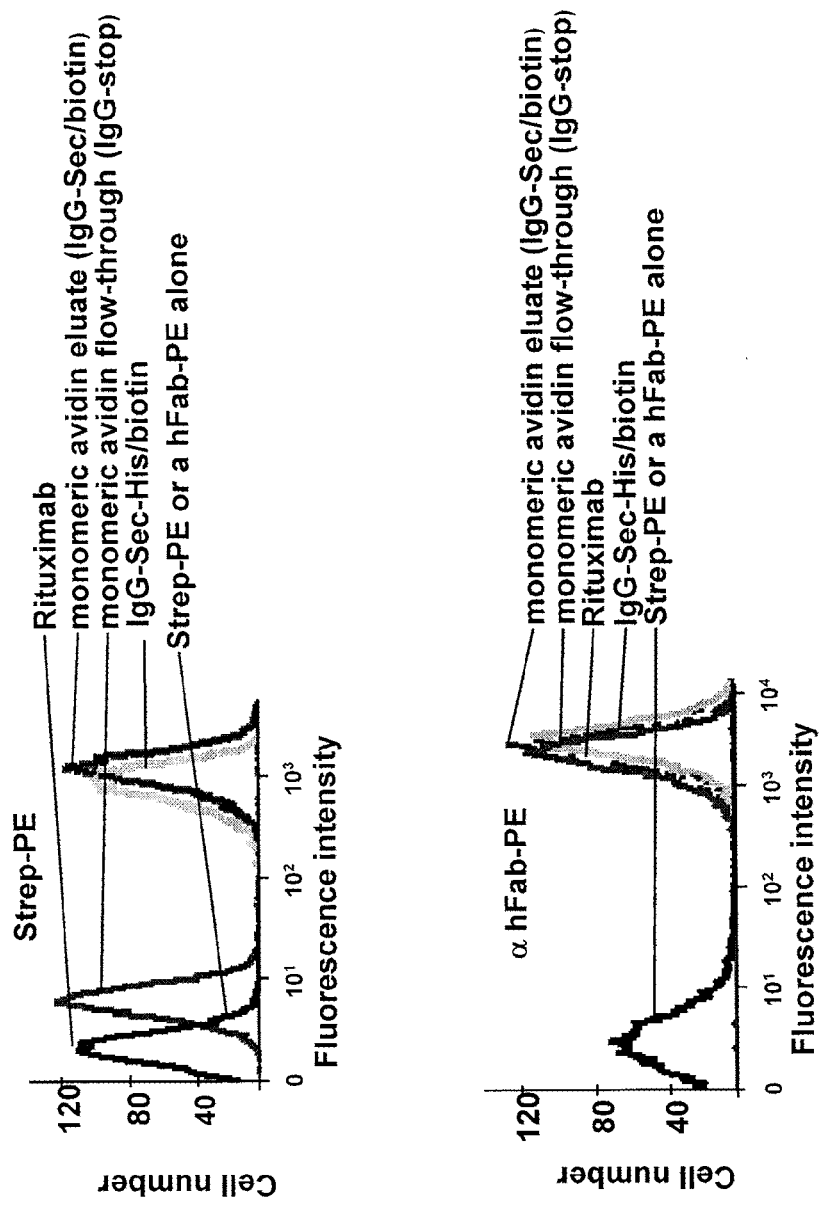

FIG. 15 is a flow cytometry plot of Rituxi-Sec (without His tag) as compared to Rituxi-stop as separated by monomeric avidin affinity chromatography. Rituxi-Sec-His/biotin and Rituximab served as controls. Only the heavy chain (~50 kDa) of IgGSec/biotin and IgG-Sec-His/biotin was biotinylated, confirming selective conjugation at the Sec interface.

Figure 16A:
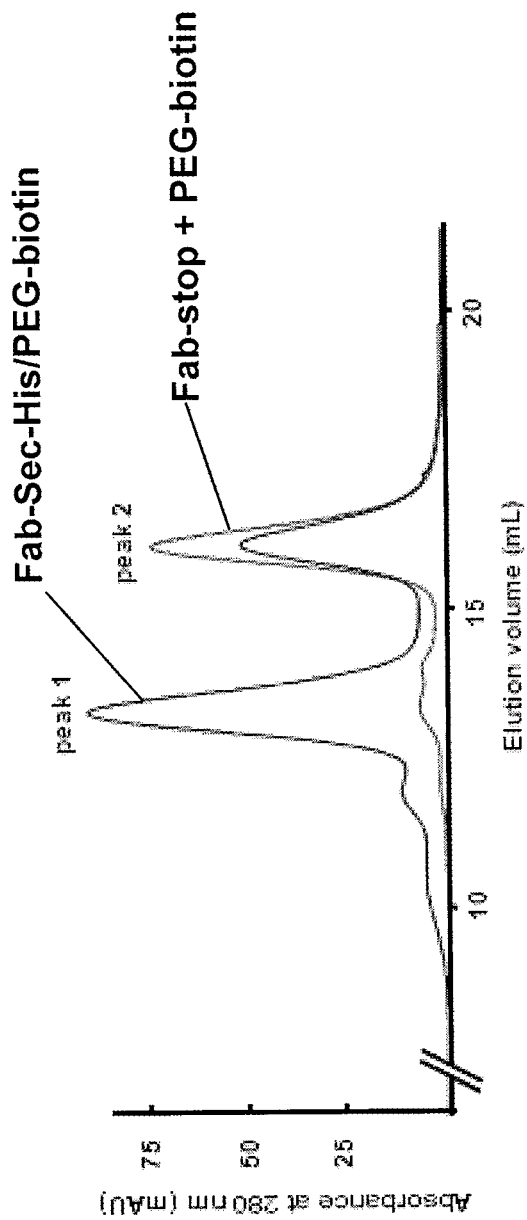

FIG. 16A is a size-exclusion chromatography plot showing conjugated (peak 1) and unconjugated (peak 2) Rituxi-Fab-Sec-His. Rituxi-Fab-stop subjected to the same conjugation and separation conditions was included for comparison.

Figure 16B:
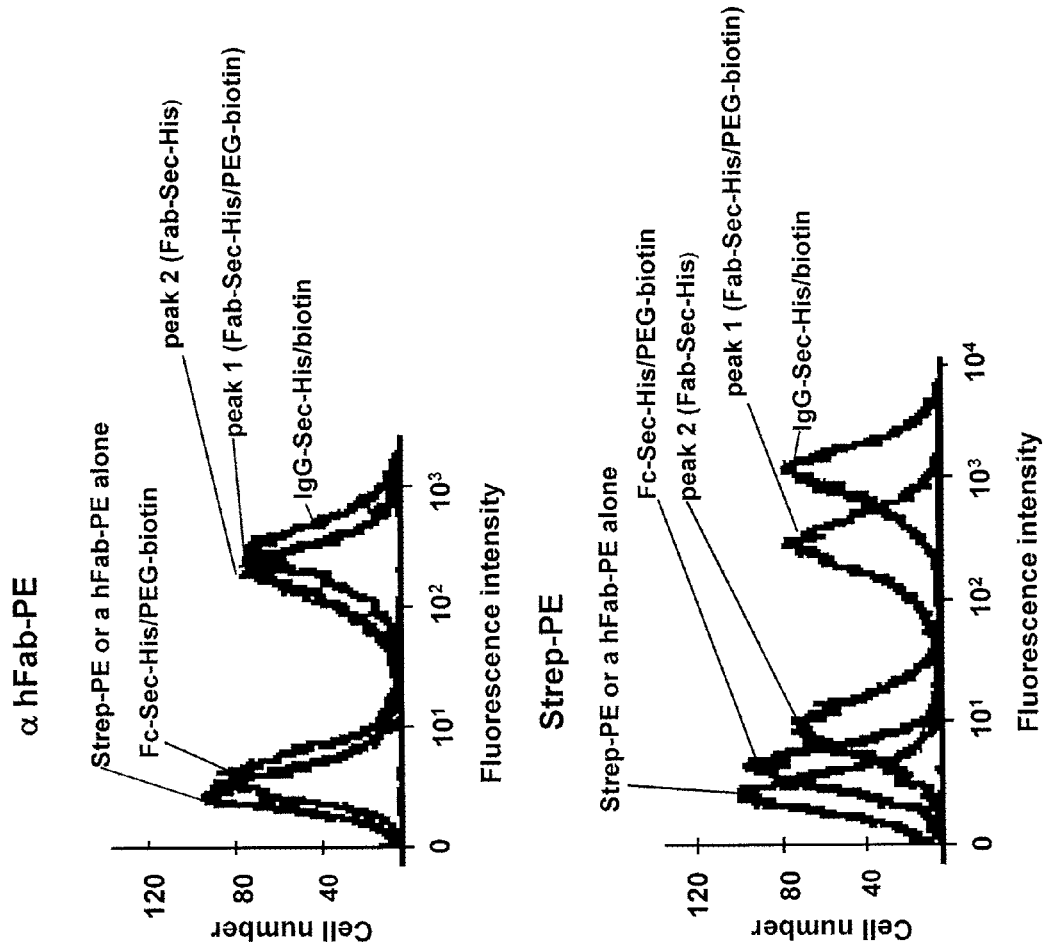

FIG. 16B is a flow cytometry plot of the separated fractions (peak 1 and peak 2). Rituxi-Sec-His/Biotin and Fc-Sec-His/PEG-biotin served as controls.

Figure 16C:
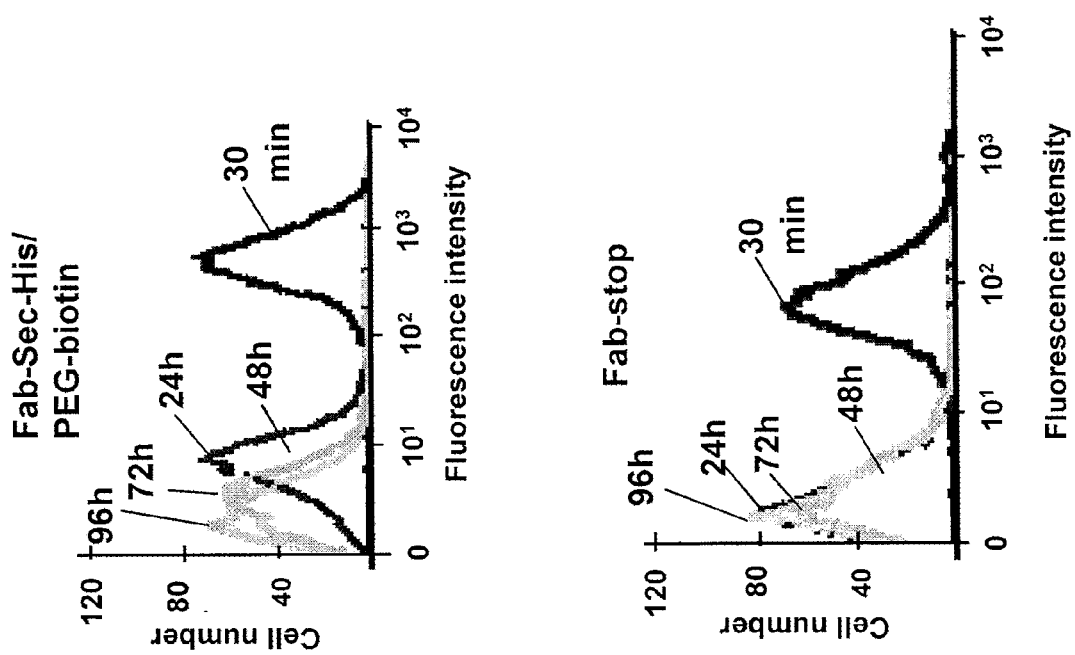

FIG. 16C is a flow cytometry plot of serum levels of Rituximab, Rituxi-Fab-Sec-His/PEGbiotin, and Fab-Stop at 30 min, 24 hours, 48 hours, 72 hours, and 96 hours. Typical results based on three individual mice in each treatment group are shown.

Figure 17:
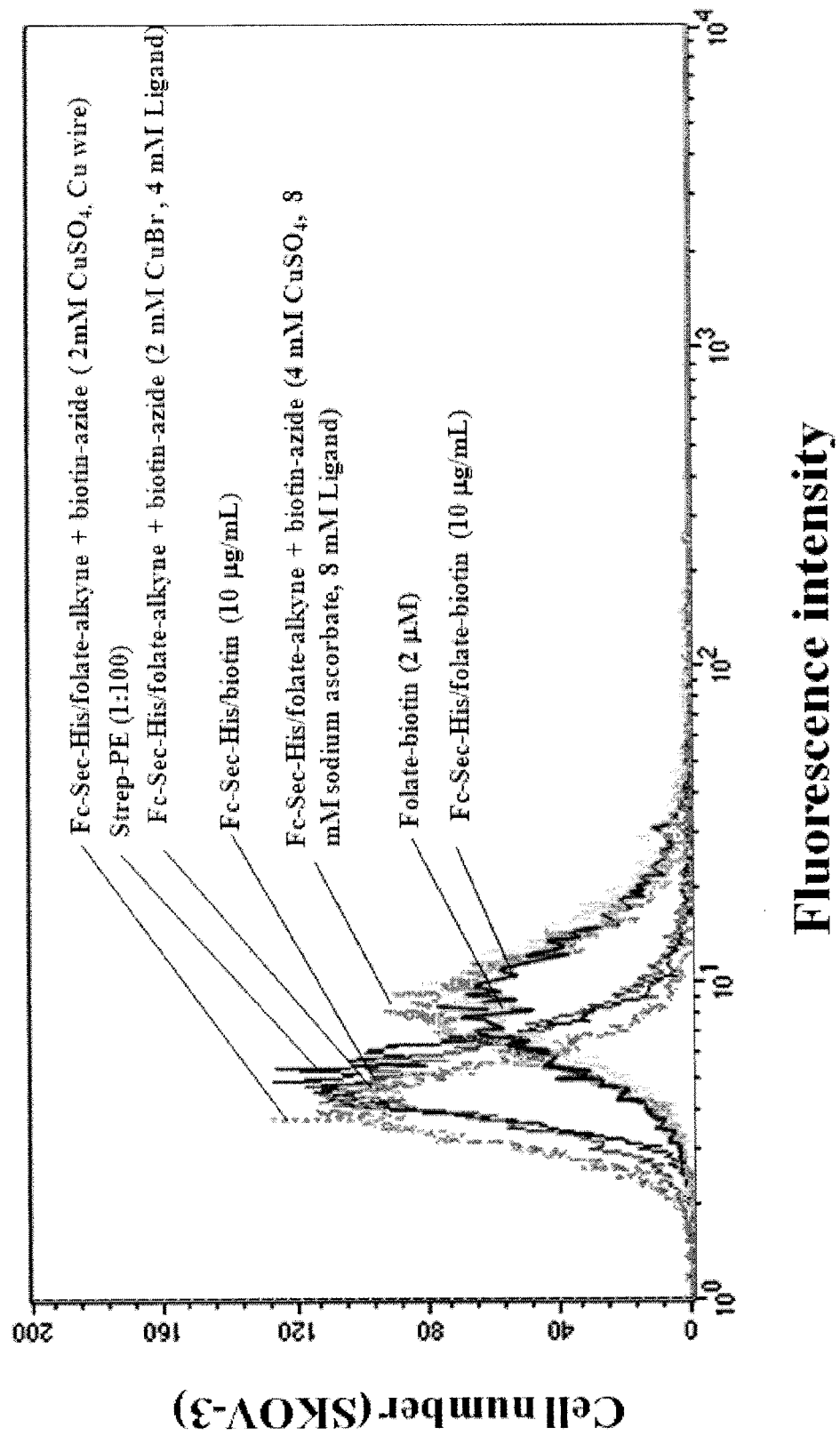

FIG. 17 is a flow cytometry plot of Fc-Sec-His/Folate as compared to Fc-biotin and Folate-biotin.

Figure 18:
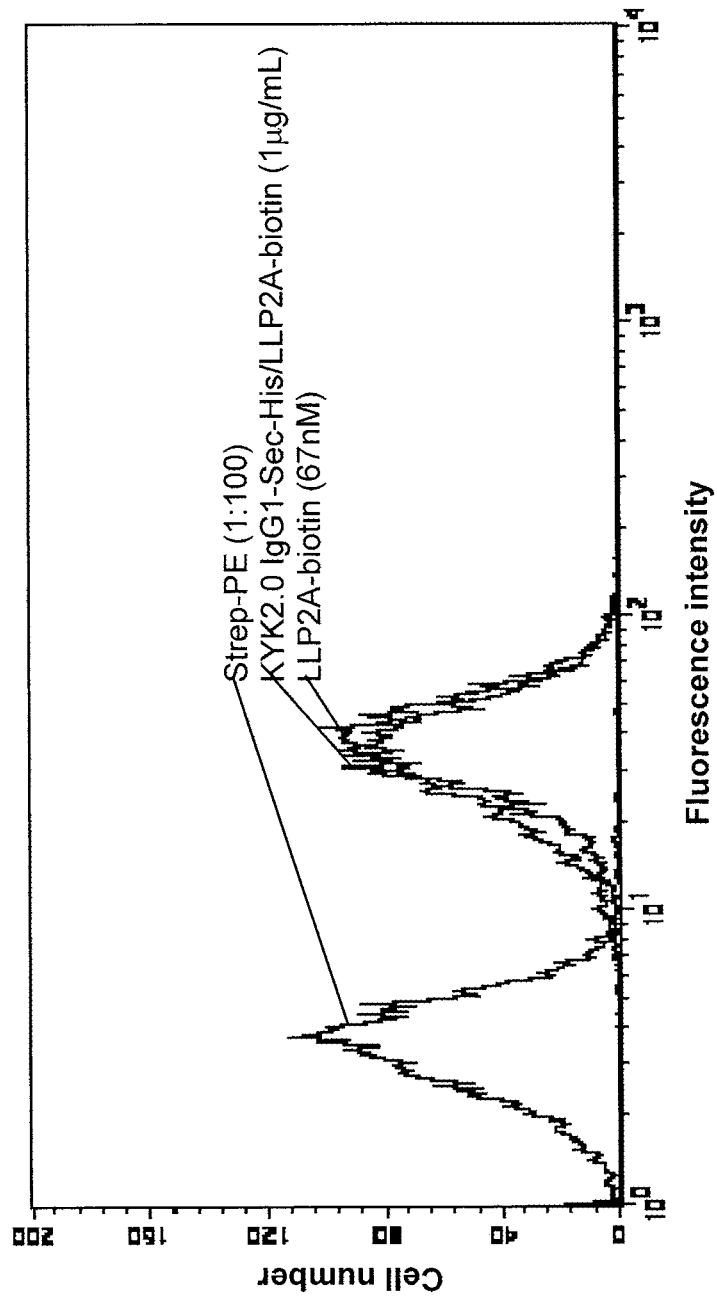

FIG. 18 is a flow cytometry plot of KYK2.0 IgG-Sec-His/LLP2A-biotin as compared to LLP2A-biotin and negative controls.

DETAILED DESCRIPTION OF THE INVENTION

The invention provides a hybrid molecule of a synthetic molecule and antibody or antibody fragment comprising a selenocysteine residue, wherein the synthetic molecule is covalently linked to the antibody or antibody fragment at the selenocysteine residue. The invention also provides a composition comprising a pharmaceutically acceptable carrier.

The antibody or antibody fragment comprises one or more selenocysteine residues. Selenocysteine is a cysteine residue analog with a selenium-containing selenol group in place of the sulfur-containing thiol group in cysteine. Although cysteine and selenocysteine are related amino acids and can undergo many of the same reactions, selenols are thought to be more reactive than thiols. The selenol of free selenocysteine has a pKa of 5.2, while the thiol of free cysteine has a pKa of 8.3. Without being bound by any particular theory, it is thought that, by controlling the pH of the alkylation reaction, selenocysteine may be selectively alkylated while leaving cysteine residues unaffected. See, e.g., Johansson et al., *Nature Methods*, 1: 1-6 (2004).

In some embodiments, the antibody or antibody fragment comprises exactly one selenocysteine residue. In other embodiments, the antibody or antibody fragment comprises more than one selenocysteine residue. The antibody or antibody fragment can comprise 1, 2, 3, 4, 5, 6, 7, 8, 9, 10 or more, 20 or more, 30 or more, 40 or more, 50 or more, or 100 or more selenocysteine residues. It is expected that the antibody or antibody fragment will usually comprise fewer than 500 selenocysteine residues.

It is believed that selenocysteine is cotranslationally incorporated at a predefined UGA stop codon that has been recoded from termination to selenocysteine insertion. In native mammalian proteins containing selenocysteine, recoding of UGA from a stop to a selenocysteine is believed to require specific secondary structures in the 3' untranslated region of the mRNA, termed "selenocysteine insertion sequence (SECIS) elements," as well as a unique tRNA, a SECIS binding protein and a specialized elongation factor. Kruyukov et al., *Science*, 300: 1439-1443 (2003). Accordingly, it is preferred that the selenocysteine residue is located near the C terminus of the translated protein. In some embodiments, the selenocysteine residue can be located within 200 amino acids of the C-terminus of the antibody or antibody fragment. In other embodiments, the selenocysteine residue can be located within 100 amino acids of the C-terminus of the antibody or antibody fragment. In still other embodiments, the selenocysteine residue can be located within 50, 40, 30, 25, 20, 19, 18, 17, 16, 15, 14, 13, 12, 11, 10, 9, 8, 7, 6, 5, 4, 3, or 2 amino acids of the C-terminus of the antibody or antibody fragment. The selenocysteine residue can also be located at the C-terminus of the antibody or antibody fragment.

The antibody can be any antibody, including without limitation, IgA, IgD, IgE, IgG, and IgM. The antibody fragment can be Fc, F(a')$_2$, Fv, scFv, IgGΔCH$_2$, minibody (also designated scFv$_2$CH$_3$), Fab, V$_L$, V$_H$, tetrabody (also designated scFv4), triabody (also designated scFv3), diabody (also designated scFv2), dsFv, or scFv-Fc. Without being bound by any particular theory, it is thought that antibodies or antibody fragments may be capable of inhibiting protein-protein interactions, which are frequently involved in the pathogenesis of cancer progression. Additionally, or alternatively, antibodies may act through multiple mechanisms including target binding as well as activation of effector functions such as complement-dependent cytotoxicity (CDC) and antibody-dependent cellular cytotoxicity (ADCC). In a particularly preferred embodiment, the antibody is a therapeutically active antibody, such as Rituximab (RITUXAN®). In other embodiments, the antibody is a fully human antibody such as KYK2.0, described in Kwong et al., *J. Mol. Biol.*, 384: 1143-56 (2008).

In a preferred embodiment, the antibody fragment is an Fc fragment, also called an Fc protein or an Fc domain. As used herein, the term "antibody protein" can encompass both antibodies and antibody fragments.

The antibody or antibody fragment can be produced using any suitable eukaryotic expression system. In a preferred embodiment, the antibody or antibody fragment is produced using a mammalian expression system.

The synthetic molecule can be any suitable synthetic molecule. While the synthetic molecule can have any suitable size (e.g., molecular weight), generally the synthetic molecule will be relatively small and will have a molecular weight of about 5000 Daltons or less, e.g., 4000 Daltons or less, 3000 Daltons or less, 2000 Daltons or less, or 1000 Daltons or less.

The synthetic molecule can include any alkylating electrophile. In some embodiments, the synthetic molecule comprises an iodoacetamide, bromoacetamide, chloroacetamide, maleimide, or acrylamide moiety. In a preferred embodiment, the synthetic molecule comprises a maleimide moiety.

The synthetic molecule can further comprise a binding moiety for a target such as a cell surface receptor. In some embodiments, the target can be an integrin such as $\alpha_4\beta_1$, $\alpha_4\beta_7$, $\alpha_v\beta_3$, $\alpha_v\beta_5$, $\alpha_v\beta_6$, $\alpha_5\beta_1$, $\alpha_{IIB}\beta_3$. The target can also be a receptor of CCR5, LHRH, CXCR4, TPO, folate, endothelin, or vitamin B12. In a preferred embodiment, the synthetic molecule can comprise a binding moiety for an integrin-binding receptor. In a more preferred embodiment, the synthetic molecule comprises both an $\alpha_4\beta_1$ and an $\alpha_4\beta_7$ integrin binding moiety.

In some embodiments, the synthetic molecule comprises a marker to facilitate identification of the hybrid molecules. In some preferred embodiments, the marker comprises a biotin moiety. In other preferred embodiments, the marker can comprise a radioisotope, a fluorescent moiety, or a luminescent moiety.

In some preferred embodiments, the synthetic molecule comprises an $\alpha4\beta1$ integrin binding moiety, a biotin moiety, and a maleimide moiety. In a particularly preferred embodiment, the $\alpha4\beta1$ integrin binding moiety can be LLP2A.

The synthetic molecule can additionally or alternatively comprise a cytotoxic agent. The cytotoxic agent can be any suitable cytotoxic agent, and many such cytotoxic agents are known to one of ordinary skill in the art. For example, the cytotoxic agent can be an alkylating agent, an antimetabolite, a natural cytotoxic product or derivative thereof, a microtubule affecting agent, and the like.

Alkylating agents useful as cytotoxic agents can be, without limitation, nitrogen mustards, ethylenimine derivatives, alkyl sulfonates, nitrosoureas, and triazenes), such as Uracil mustard, Chlormethine, Cyclophosphamide (CYTOXAN®), Ifosfamide, Melphalan, Chlorambucil, Pipobroman, Triethylene-melamine, Triethylenethiophosphoramine, Busulfan, Carmustine, Lomustine, Streptozocin, Dacarbazine, Temozolomide, and the like.

Antimetabolites useful as cytotoxic agents can be, without limitation, folic acid antagonists, pyrimidine analogs, purine analogs, and adenosine deaminase inhibitors, such as Methotrexate, 5-Fluorouracil, Floxuridine, Cytarabine, 6-Mercaptopurine, 6-Thioguanine, Fludarabine phosphate, Pentostatine, Gemcitabine, and the like.

Natural products and their derivatives useful as cytotoxic chemotherapy can be, without limitation, vinca alkaloids, antitumor antibiotics, enzymes, lymphokines and epipodophyllotoxins, including Vinblastine, Vincristine, Vindesine, Bleomycin, Dactinomycin, Daunorubicin, Doxorubicin, Epirubicin, Idarubicin, Ara-C, paclitaxel (TAXOL®) Mithramycin, Deoxyco-formycin, Mitomycin-C, L-Asparaginase, Interferons (especially IFN-a), Etoposide, Teniposide, calicheamicin, maytansinoid, and the like.

Anti-proliferative agents useful as cytotoxic agents can include navelbene, CPT-11, anastrazole, letrazole, capecitabine, reloxafine, cyclophosphamide, ifosamide, and droloxafine. Preferred classes of antiproliferative cytotoxic agents are the EGFR inhibitors, Her-2 inhibitors, and CDK inhibitors. Some preferred anti-proliferative cytostatic agents are paclitaxel, cis-platin, carboplatin, epothilones, gemcytabine, CPT-11,5-fluorouracil, tegafur, leucovorin, and EGFR inhibitors such as IRESSA® (ZD 1839, 4-(3-chloro-4-fluorophenylamino)-7-methoxy-6-(3-(4-morpholinyl)propoxy)quinazoline and OSI-774 (4-(3-ethynylphenylamino)-6,7-bis(2-methoxyethoxy)quinazoline).

Microtubule affecting agents useful as cytotoxic agents include, but are not limited to, allocolchicine (NSC 406042), Halichondrin B (NSC 609395), colchicine (NSC 757), colchicine derivatives (e.g., NSC 33410), dolastatin 10 (NSC 376128), maytansine (NSC 153858), rhizoxin (NSC 332598), paclitaxel (TAXOL® NSC 125973), paclitaxel derivatives (e.g., derivatives (e.g., NSC 608832), thiocolchicine (NSC 361792), trityl cysteine (NSC 83265)), vinblastine sulfate (NSC 49842), vincristine sulfate (NSC 67574), natural and synthetic epothilones including but not limited to epothilone A, epothilone B, auristatin, and discodermolide (see Service, *Science,* 274: 2009 (1996)) estramustine, nocodazole, MAP4, and the like. Examples of such agents are also described in the scientific and patent literature, see, e.g., Bulinski, *J. Cell Sci.,* 110: 3055-3064 (1997); Panda, *Proc. Natl. Acad. Sci. USA,* 94: 10560-10564 (1997); Muhlradt, *Cancer Res.,* 57: 3344-3346 (1997); Nicolaou, *Nature,* 387: 268-272 (1997); Vasquez, *Mol. Biol. Cell.,* 8: 973-985 (1997); Panda, *J. Biol. Chem.,* 271: 29807-29812 (1996).

Microtubule affecting agents useful as cytotoxic agents include, but are not limited to, microtubule-stabilizing agents such as paclitaxel, docetaxel (TAXOTERE®), 7-O-methylthiomethylpaclitaxel (disclosed in U.S. Pat. No. 5,646,176), 4-desacetyl-4-methylcarbonatepaclitaxel, C-4 methyl carbonate paclitaxel (disclosed in International Patent Application Publication WO 94/14787), epothilone A, epothilone B, epothilone C, epothilone D, desoxyepothilone A, desoxyepothilone B, and derivatives thereof, as well as microtubule-disruptor agents.

Additional suitable cytotoxic agents include melphalan, hexamethyl melamine, thiotepa, cytarabin, idatrexate, trimetrexate, dacarbazine, L-asparaginase, camptothecin, topotecan, bicalutamide, flutamide, leuprolide, pyridobenzoindole derivatives, interferons, and interleukins.

Most preferably, the cytotoxic agent is a moiety that is known or in clinical use when conjugated to an antibody, such as the moieties bound to the antibodies used in ibritumomab tiutiuxetan (ZEVALIN®), tositumomab-[131]I (BEXXAR®), and gemtuzumab ozogamicin (MYLOTARG®).

The invention further provides a method of inhibiting cell surface receptor binding in cells. The method comprises contacting cells with the hybrid molecule, i.e., the hybrid molecule as described herein which comprises an antibody or antibody fragment and a synthetic molecule, wherein the antibody or antibody fragment comprises a selenocysteine residue, and wherein the synthetic molecule is covalently linked to the antibody or antibody fragment at the selenocysteine residue. The cells are contacted directly with the inventive composition comprising the hybrid molecule and a pharmaceutically acceptable carrier.

The cells can be any cells having cell surface receptors. In a preferred embodiment, the cells are human peripheral blood mononuclear cells (PBMC), leukocytes (lymphocytes and myelocytes), endothelial cells, or tumor cells. The cells can be either malignant or non-malignant. The cells can be metastatic or non-metastatic.

Preferably, the cells are located in a patient. The cells can also be in vitro. In other aspects, the cells can be in a tissue sample taken from the patient. The patient is preferably a mammal, and more preferably a human of any age or sex.

The inventive methods can be used to treat any patient afflicted with a condition that can benefit from administration of the inventive composition to the patient. Such conditions include cancer, infectious diseases, inflammatory diseases, and autoimmune diseases. In some embodiments, the cancer is a hematologic malignancy or a solid malignancy. The cancer can be leukemia, such as acute myelogenous leukemia (AML) or chronic lymphocytic leukemia (CLL). In other embodiments, the condition is an autoimmune disease such as multiple sclerosis, or acute or chronic graft-versus-host (GVH) disease.

In addition, the invention provides a method of preparing the hybrid molecule comprising a synthetic molecule and an antibody or an antibody fragment. The method comprises (i) providing a gene encoding an antibody or an antibody fragment comprising an Fc domain, wherein the gene comprises (a) a UGA codon in the region encoding the Fc domain, and (b) a SECIS element; (ii) expressing the gene in a mammalian expression system, in a medium including sodium selenite, to produce the antibody or the antibody fragment; (iii) purifying the antibody or antibody fragment; and (iv) incubating the antibody or antibody fragment with the synthetic molecule, a buffer, and a reducing agent to produce the hybrid molecule comprising the synthetic molecule and the antibody or antibody fragment.

Figure 1:
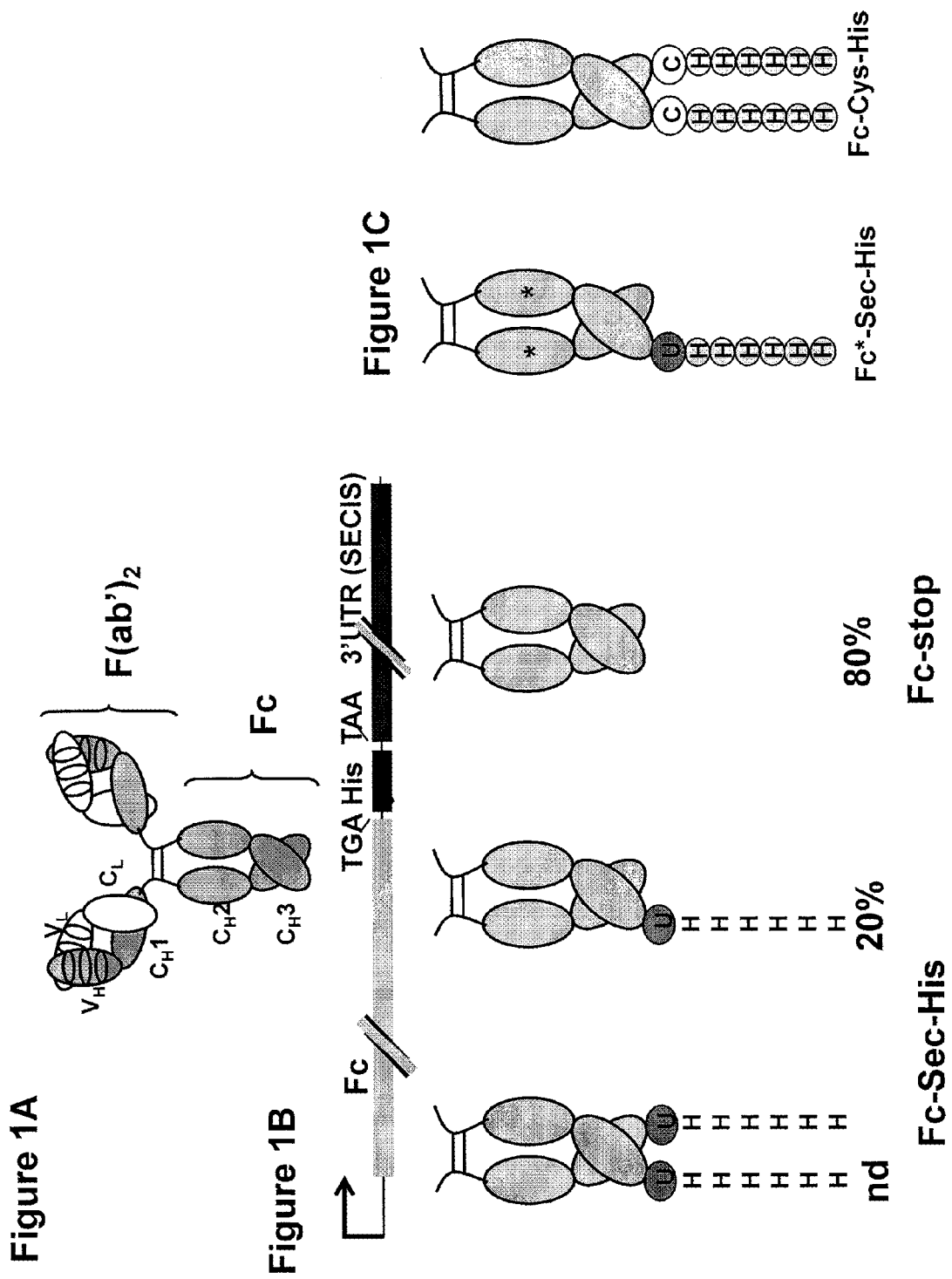
FIG. 1C is a schematic representation of an antibody protein produced using the expression cassette shown in FIG. 1B along with an antibody protein produced using a similar but modified expression cassette, wherein an Fc protein is produced with a cysteine in the position of the selenocysteine (Fc-Cys-His) and with a N297A mutation that diminishes Fc receptor interactions (Fc*-Sec-His).

A schematic representation of a gene that can be used in the production methods of the invention is provided in FIG. 1B. It is generally preferred that the UGA codon, which is the codon used to encode selenocysteine, is inserted near the 3' end of the translated region of the gene. Without being bound by any particular theory, it is thought that the likelihood of successful translation of the UGA stop codon to a selenocysteine is increased by relative proximity of the UGA codon to the SECIS element. Preferably, the UGA codon is located within about 1000 nucleotides of the 3' end of the translated region. More preferably, the UGA codon is located within about 800, 700, 600, 500, 400, 300, 200, 150, 120, 90, 75, 60, 50, 40, 30, 20, 10, 9, or 6 codons of the 3' end of the translated region. Alternatively, the UGA codon can be the final codon of the 3' translated region.

The selenocysteine-containing antibody protein can be expressed in any suitable eukaryotic expression system. Preferably, a mammalian expression system is used, although one of ordinary skill in the art can select any naturally occurring or modified expression system able to supply selenocysteine tRNA, a SECIS binding protein, and the specialized elongation element required for successful selenocysteine transcription. Preferably, sodium selenite ($Na_2SeO_3$) is added to the culture medium, although one of ordinary skill in the art will understand that other selenium supplementation can also be used.

The selenocysteine-containing antibody protein can be purified by any method known to one of skill in the art. For example, protein G affinity chromatography or immobilized metal affinity chromatography (IMAC) can be used, as described in Harlow and Lane (1988), *Antibodies: A Laboratory Manual*, Cold Spring Harbor Laboratory, Cold Spring Harbor, N.Y. See also Terpe (2003), *Appl. Microbiol. Biotechnol.* 60, 523-533.

To conjugate the selenocysteine-containing antibody protein to the synthetic molecule, the protein can be incubated with the synthetic molecule in the presence of a reducing agent and a buffer. The pH of the incubation solution is preferably maintained between about 3 and about 7, preferably about 4 to about 6, more preferably at about 5. In some embodiments, the pH of the incubation solution is approximately 5.2. The reducing agent can be any reducing agent such as DTT. The synthetic molecule is preferably provided in at least a 3-fold excess to the selenocysteine-containing antibody protein. One of ordinary skill in the art will also understand that reaction conditions can be modified or optimized to the synthetic molecule, if necessary.

The composition of the invention desirably comprises a pharmaceutically acceptable carrier. The pharmaceutically acceptable carrier can be any suitable pharmaceutically acceptable carrier. The term "pharmaceutically acceptable carrier" as used herein means one or more compatible solid or liquid fillers, diluents, other excipients, or encapsulating substances which are suitable for administration into a human or veterinary patient. The term "carrier" denotes an organic or inorganic ingredient, natural or synthetic, with which the active ingredient is combined to facilitate the application. The pharmaceutically acceptable carrier can be co-mingled with one or more of active components, e.g., the hybrid molecule, and with each other, when more than one pharmaceutically acceptable carrier is present in the composition in a manner so as not to substantially impair the desired pharmaceutical efficacy. "Pharmaceutically acceptable" materials are capable of administration to a patient without the production of significant undesirable physiological effects such as nausea, dizziness, rash, or gastric upset. It is, for example, desirable for a composition comprising a pharmaceutically acceptable carrier not to be immunogenic when administered to a human patient for therapeutic purposes.

The pharmaceutical composition can contain suitable buffering agents, including, for example, acetic acid in a salt, citric acid in a salt, boric acid in a salt, and phosphoric acid in a salt. The pharmaceutical compositions also optionally can contain suitable preservatives, such as benzalkonium chloride, chlorobutanol, parabens, and thimerosal.

The pharmaceutical composition can be presented in unit dosage form and can be prepared by any suitable method, many of which are well known in the art of pharmacy. Such methods include the step of bringing the active agent into association with a carrier that constitutes one or more accessory ingredients. In general, the composition is prepared by uniformly and intimately bringing the hybrid molecule into association with a liquid carrier, a finely divided solid carrier, or both, and then, if necessary, shaping the product.

A composition suitable for parenteral administration conveniently comprises a sterile aqueous preparation of the inventive composition, which preferably is isotonic with the blood of the recipient. This aqueous preparation can be formulated according to known methods using suitable dispersing or wetting agents and suspending agents. The sterile injectable preparation also can be a sterile injectable solution or suspension in a non-toxic parenterally-acceptable diluent or solvent, for example, as a solution in 1, 3-butane diol. Among the acceptable vehicles and solvents that can be employed are water, Ringer's solution, and isotonic sodium chloride solution. In addition, sterile, fixed oils are conventionally employed as a solvent or suspending medium. For this purpose any bland fixed oil can be employed, such as synthetic mono- or di-glycerides. In addition, fatty acids such as oleic acid can be used in the preparation of injectables. Carrier formulations suitable for oral, subcutaneous, intravenous, intramuscular, etc. administrations can be found in *Remington's Pharmaceutical Sciences*, Mack Publishing Co., Easton, Pa., which is incorporated herein in its entirety by reference thereto.

The delivery systems useful in the context of the invention include time-released, delayed release, and sustained release delivery systems such that the delivery of the inventive composition occurs prior to, and with sufficient time to cause, sensitization of the site to be treated. The inventive composition can be used in conjunction with other therapeutic agents or therapies. Such systems can avoid repeated administrations of the inventive composition, thereby increasing convenience to the subject and the physician, and may be particularly suitable for certain compositions of the invention.

Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are lipids including sterols such as cholesterol, cholesterol esters, and fatty acids or neutral fats such as mono-di- and tri-glycerides; hydrogel release systems; sylastic systems; peptide based systems; wax coatings; compressed tablets using conventional binders and excipients; partially fused implants; and the like. Specific examples include, but are not limited to: (a) erosional systems in which the active composition is contained in a form within a matrix such as those described in U.S. Pat. Nos. 4,452,775, 4,667,014, 4,748,034, and 5,239,660 and (b) diffusional systems in which an active component permeates at a controlled rate from a polymer such as described in U.S. Pat. Nos. 3,832,253 and 3,854,480. In addition, pump-based hardware delivery systems can be used, some of which are adapted for implantation.

The following examples further illustrate the invention but, of course, should not be construed as in any way limiting its scope.

EXAMPLE 1

This example demonstrates that selenocysteine can be incorporated into an antibody molecule expressed in mammalian cells.

Preparing a Plasmid.

The Fc portion of human IgG1 including the hinge region was amplified by PCR using the previously described PIGG vector as a template, described in Rader et al., *FASEB J.*, 16: 2000-2002 (2002), and the following primers: Fc-5' (gggtaccatggactggacctggaggatcctct-tcttggtggcagcagccacaggagct-cactccgagcccaaatcttctgacaaaactcacaca) (SEQ ID NO:1) and Fc-3' (cggagacaagcttaggctcttctgcgtgtagtggttgtgcag) (SEQ ID NO:2). The 5' primer fuses the human IgG1 signal sequence to Fcγ1, thereby enabling the expressed Fc-protein to be secreted into the medium. Cysteine 5 in the γ1 hinge (EPKS CDKTHTCPPCP) (SEQ ID NO:3) forming a disulfide bridge with a cysteine in constant region of the light chain was mutated to a serine as described in Lo et al., *Protein Eng.*, 6: 495-500 (1998). A silent Hind III site was introduced through the 3' primer, replacing the codons of leucine 121, serine 122, and leucine 123 in the C-terminus (119 KSLSLSPGK 130) (SEQ ID NO:18) of the γ1 CH$_3$ domain upstream of the natural stop codon without changing the amino acid sequence. The isolated PCR fragment was cloned into pCEP4 vector (Invitrogen) by KpnI/HindIII-ligation, thereby deleting the last 4 codons of the γ1 CH$_3$ domain including the stop codon. This construct, termed pCEP-Fc, served as parental template for all further Fc-constructs.

This Fc construct was then modified by the incorporation of a selenocysteine and an adjacent (His)$_6$ tag at the C-terminus of Fc. A PCR fragment containing the last 4 codons of Fc, the selenocysteine-encoding opal stop codon TGA, 6 histidine codons, the ochre stop codon TAA, and a portion of the 3'-untranslated region (UTR) of the thioredoxin reductase 1 (TrxR1) (described in Nalvarte et al., *J. Biol. Chem.*, 279: 54510-54517 (2004) gene was synthesized using human genomic DNA as a template.

An internal HindIII site in the TrxR1 3' untranslated region was deleted by site-directed mutagenesis: First, two individual PCR fragments were amplified using the following primer pairs: Fc-Sec-His 5' (gcctaagcttgtctccgggtgcctgacatcaccatcaccatcactaagccccagtgtggatgctgttg) (SEQ ID NO:4) and HindIII deletion 3' (agaagctccaagaactgctggcag) (SEQ ID NO:5) as well as HindIII deletion 5' (cctgccagcagttcttggagcttct) (SEQ ID NO:6) and Fc-Sec-His 3' (agct ctcgaggccaaatgagatgaggacgtgag) (SEQ ID NO:7). In a second step, the fragments were assembled by PCR amplification and the resulting fragment was HindIII/XhoI-digested and cloned into pCEP-Fc resulting in pCEP-Fc-Sec-His. In the control plasmid pCEP-Fc-Cys-His, the selenocysteine codon was replaced by the cysteine-encoding triplet TGC using the primer Fc-Cys-His 5' (gcctaagcttgtctccgggtgcc tgccatcaccatcaccatcactaagccccagtgtggatgctgttg) (SEQ ID NO:8).

For the analysis of selenocysteine incorporation by mass spectrometry, an additional arginine codon was inserted between the opal stop codon and the His tag. The additional arginine enabled the cleavage of the His tag during the in-gel trypsin digestion necessary for mass spectrometric analysis. This construct was generated by replacing the Fc-Sec-His 5' primer with Fc-Sec-Arg-His 5' (gcctaagcttgtctccgggtgcctga cggcatcaccatcaccatcactaagccccagtgtggatgctgttg) (SEQ ID NO:9), resulting in pCEP-Fc-Sec-Arg-His.

Plasmid pCEP-Fc*-Sec-His, a pCEP-Fc-Sec-His-derived construct carrying the mutation N297A, was generated using the following primers pairs: (a) 5'Primer N297A (aggagcagtacgccagcacgtaccgtgtggt) (SEQ ID NO:10) and EBV reverse (gtggtttgtccaaactcatc; Invitrogen) (SEQ ID NO:11), and (b) 3'Primer N297A (accacacggtacgtgctggcgtactgctcct) (SEQ ID NO:12) and pCEP forward (agcagagctcgtttagtgaaccg; Invitrogen) (SEQ ID NO:13). The amplified fragments were assembled by PCR amplification, and the resulting fragment was KpnI/XhoI-digested and cloned into pCEP-Fc resulting in pCEP-Fc*-Sec-His.

Expression of a Sec Protein.

The plasmids described above were transiently transfected into HEK 293F cells (Invitrogen) with 293fectin (Invitrogen) using conditions detailed in the manufacturer's protocol. Transfected HEK 293F cells were cultured in FreeStyle serum-free medium (Invitrogen), supplemented with 1 μM sodium selenite (Na$_2$SeO$_3$), in spin flasks (Integra Biosciences, Switzerland) under constant rotation at 75 rpm in a humidified atmosphere containing 8% CO$_2$ at 37° C.

Purifying a Sec Protein.

Three days after transfection, the medium was collected after centrifugation, replaced for two additional days, and collected again. The combined supernatants were filtered through a 0.45-μm membrane and tenfold concentrated using an ultrafiltration device with a 10-kDa cutoff membrane (Millipore). The concentrate was 1:1 diluted with phosphate-buffered saline (PBS) and loaded on a 1-mL recombinant Protein G HiTrap column (GE Healthcare). PBS was used for column equilibration and washing, 0.5 M acetic acid (pH 3.0) was used for elution, and 1 M Tris-HCl (pH 8.0) was used for immediate neutralization. The neutralized eluate was dialyzed at 4° C. overnight against PBS using Slide-A-Lyzer cassettes with 10-kDa cutoff (Pierce) and concentrated with 10-kDa cutoff centrifugal filter devices (Millipore). In order to separate Fc-Sec-His from the byproduct Fc-stop, the concentrated Fc-solution was 10× diluted in loading/washing buffer (500 mM NaCl and 25 mM imidazol in PBS) and loaded on a 1-mL HisTrap column (GE Healthcare). The flow through of the column containing the Fc-stop protein was collected. Subsequently, the column was washed with 50 mL loading/washing buffer and the bound Fc-Sec-His protein was eluted with elution buffer (500 mM NaCl and 500 mM imidazol in PBS). Both eluate and flow through were again dialyzed at 4° C. overnight against PBS using Slide-A-Lyzer cassettes with 10-kDa cutoff (Pierce) and concentrated with 10-kDa cutoff centrifugal filter devices (Millipore).

Western Blots.

Western blots were performed on the concentrated supernatant to confirm the incorporation of selenocysteine into the Fc protein, based on detection of the histidine tag. Purified protein (1 µg) or concentrated culture supernatant (50 µL of 10× concentrated) was electrophoresed on a NuPage 4-12% gradient gel (Invitrogen), blotted on a nitrocellulose membrane (GE Healthcare), and blocked with Western Blocking Reagent (Roche). Fc protein without the selenocysteine and histidine tag (Fc-stop) was used as a control.

To detect Fc-Sec-His, that is, Fc protein in which the UGA stop codon was successfully translated as selenocysteine and followed by a histidine tag, the monoclonal mouse Pentahis antibody (Qiagen) was diluted to 1 µg/mL in Western Blocking Reagent followed by polyclonal horseradish peroxidase-coupled goat anti-mouse antibodies (Jackson ImmunoResearch Laboratories) (1:10,000). Immunoreactive bands were developed using SuperSignal West Pico Chemoluminescent Substrate (Pierce) and visualized using BioMax MR autoradiography film (Kodak). Although Fc protein was detected in both the control Fc-stop and the concentrated culture supernatant, the strong anti-histidine tag signal was only detected in the supernatant of the Fc-Sec-His transfected cells.

Autoradiography.

To confirm that selenocysteine had been incorporated, HEK 293F cells as described above were transfected with either Fc-Sec-His or Fc-Cys-His, a negative control in which the opal codon TGA of the Fc-Sec-His protein was replaced by the cysteine-encoding triplet TGC. Transfected and untransfected cells were incubated for 24 h with or without 50 mCi of [$^{75}$Se]O$_4$, radioactive selenate, in place of sodium selenite. The supernatant was harvested, concentrated, processed by electrophoresis and blotting as described above, and analyzed by radiography, results of which showed successful incorporation of selenocysteine.

Mass Spectrometry.

Figure 2:
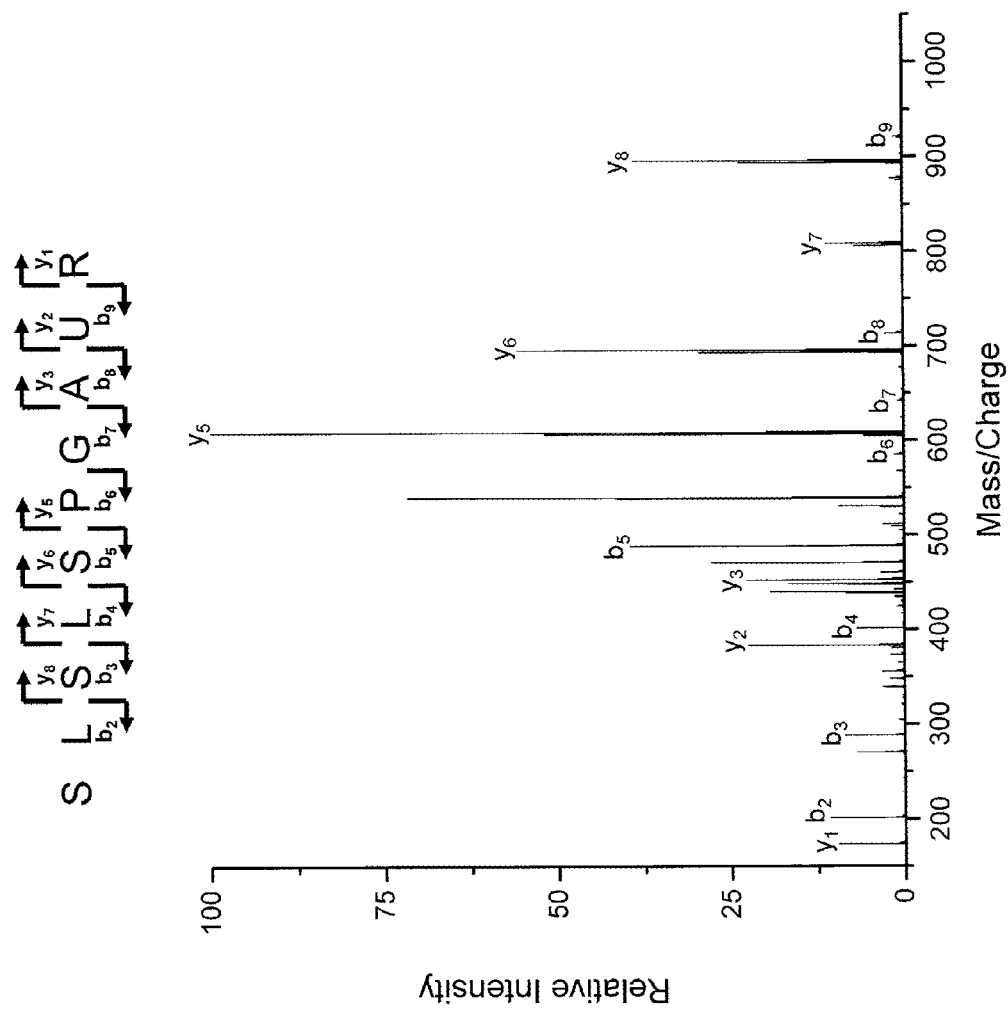
FIG. 2 is a LC-MS/MS mass spectrometry plot of purified Fc-Sec-His protein separated by non-reducing SDS-PAGE, stained with Coomassie dye, and isolated and digested with trypsin. Each peak represents a portion of the tryptic peptide SLSLSPGAUR, where U is the single letter code for selenocysteine.

Additional verification of the selenocysteine incorporation was performed using mass spectrometry on cultured protein prepared as above, but with an arginine residue inserted between the selenocysteine and the histidine tag (Fc-Sec-Arg-His). This modified protein was purified with G protein affinity chromatography and immobilized metal affinity chromatography. Tandem mass spectrometry (LC/MS-MS), results of which are shown in FIG. 2, confirmed the presence of selenocysteine (represented by the single letter designation "U") in histidine-tag purified Fc proteins.

Therefore, based on these results, selenocysteine was selectively incorporated into an antibody molecule expressed in mammalian cells.

EXAMPLE 2

This example demonstrates that a synthetic molecule can be selectively bound to a selenocysteine-containing antibody protein.

Conjugating the Small Synthetic Molecule to the Selenocysteine-Containing Antibody Protein.

A biotin reporter molecule (PEO-Iodoacetyl Biotin, molecular weight 542.43 g/mol, Pierce) was covalently attached to the selenocysteine of the Fc-Sec-His proteins described above. Fc-Sec-His and controls including Fc-stop and Fc-Cys-His were diluted in 15 mL 100 mM sodium acetate (pH 5.1) and concentrated to a 4 µM solution using 10-kDa cutoff centrifugal filter devices (Millipore). DTT (0.1 mM final concentration) as well as the biotin reporter molecule (40 µM final concentration) were added to the proteins and incubated for 50 min in the dark. The proteins were diluted in 15 mL 100 mM sodium acetate (pH 5.1) and 100× concentrated using again 10-kDa cutoff centrifugal filter devices (Millipore). The same step was repeated once with 100 mM sodium acetate (pH 5.1) and subsequently twice with PBS.

ELISA.

To confirm selective conjugation of PEO-Iodoacetyl Biotin, each well of a 96-well Costar 3690 plate (Corning) was incubated with 200 ng Fc-protein and derivatives thereof (Fc-Sec-His or Fc controls including Fc-Cys-His and Fc-stop, incubated with the biotin reporter molecule) in 25 µL PBS for 1 h at 37° C. Subsequent incubations were all for 1 h at 37° C. After blocking with 3% (w/v) BSA/PBS, either 1 µg/mL streptavidin conjugated to horseradish peroxidase (50 ng/well) or a 1:1,000 dilution of donkey anti-human IgG polyclonal antibodies conjugated to horseradish peroxidase (Jackson ImmunoResearch Laboratories) in 1% (w/v) BSA/PBS were added, incubated and washed with H$_2$O (10×200 µL/well). Colorimetric detection was performed using 2,2'-Azino-bis(3-ethylbenzthiazoline)-6-sulfonic acid (Roche) as substrate according to the manufacturer's directions. All of the Fc-containing proteins showed activity to the IgG polyclonal antibodies, but only Fc-Sec-His showed reactivity to the streptavidin.

Western Blot.

Western blots were also performed to confirm detection of iodoacetyl-coupled biotinylation of Fc-Sec-His as compared to Fc-Cys-His or Fc-stop control proteins. Using the methods described above, horseradish peroxidase-conjugated streptavidin (BD Biosciences) or horseradish peroxidase-coupled polyclonal donkey anti-human IgG antibodies (Jackson ImmunoResearch Laboratories) (both 1:1,000 diluted) in Western Blocking Reagent were used to demonstrate that the Fc-Sec-His protein was selectively biotinylated.

SDS-PAGE.

To evaluate the quantitative biotinylation of Fc-Sec-His, Fc-Sec-His and Fc-stop were incubated with the biotin reporter molecule. Both proteins were incubated separately with magnetic streptavidin beads. The supernatant and the extensively washed beads were analyzed by reducing SDS PAGE followed by staining with Coomassie dye. Fc-Sec-His bound extensively to the magnetic streptavidin beads, indicating near quantitative biotinylation, while the Fc-stop control remained in the supernatant.

These results confirm that the synthetic molecule was selectively added to the selenocysteine-containing protein

EXAMPLE 3

This example demonstrates that activity is retained in vitro for an antibody molecule bound to a synthetic small molecule.

The biotin reporting moiety described above was incubated with Fc-Sec-His along with Fc*-Sec-His and Fc*-stop, two control proteins prepared as the Fc-Sec-His and Fc-stop proteins described above but having a mutation (N297A) that impairs Fc-receptor binding. An SDS-PAGE/Coomassie analysis of Fc-Sec-His, Fc*-Sec-His, and Fc-stop showed that selenocysteine was incorporated into Fc*-Sec-His at a similar level to Fc-Sec-His, wherein Fc*-Sec-His has a lower molecular weight due to the removal of the glycosylation site in the $CH_2$ portion of the Fc protein.

Figure 3:
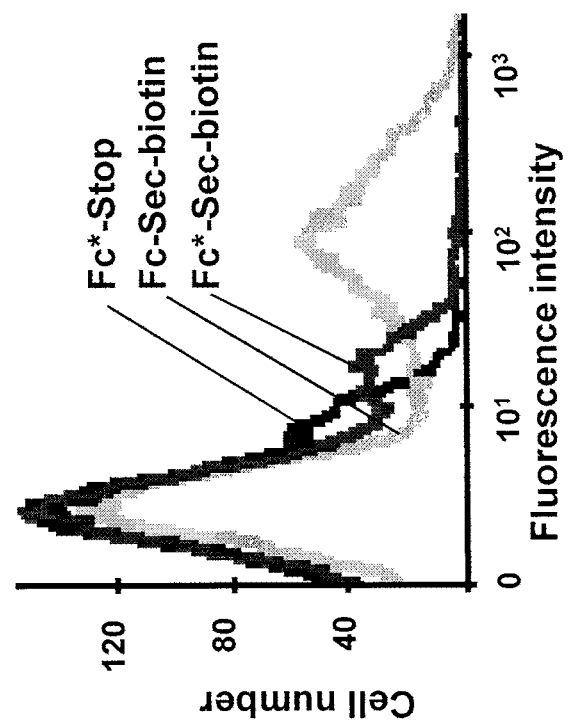
FIG. 3 is a flow cytometry plot of Fc-Sec-His after incubation with PBMC expressing the Fc receptor, as compared to Fc*-Sec-His, and Fc-stop.

Binding to peripheral blood mononuclear cells (PBMC), which express the Fc receptor, was analyzed using flow cytometry. Five μg of Fc-Sec-His, Fc*-Sec-His, and Fc*-stop were incubated with PBMC, and then stained with a streptavidin/PE conjugate. As shown in FIG. 3, the non-mutated Fc-Sec-His protein retained its ability to bind the Fc receptor even after conjugation to the biotin reporting moiety, while the mutated Fc* proteins could not bind to the Fc receptor protein regardless of selenocysteine incorporation or biotin moiety attachment.

EXAMPLE 4

This example demonstrates that activity is retained in vitro for a synthetic small molecule bound to an antibody molecule.

Figure 4:
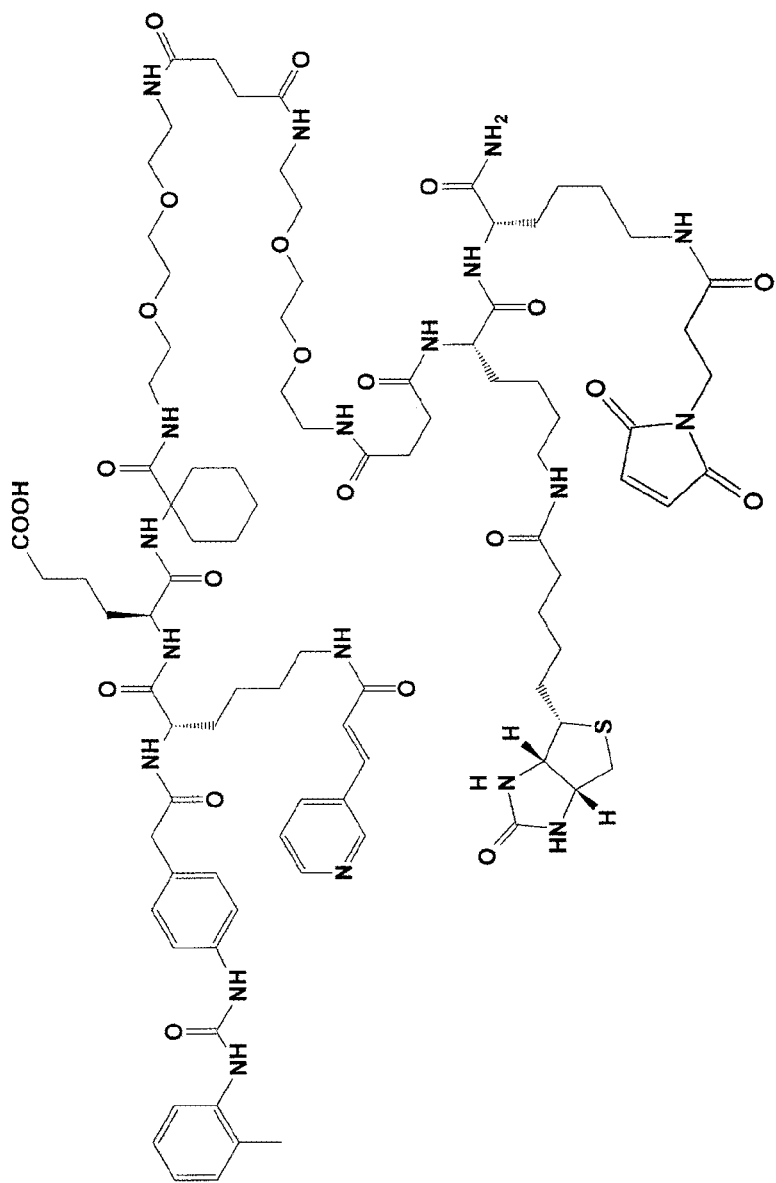
FIG. 4 depicts the chemical structure of LLP2A/biotin/maleimide, having a human integrin $\alpha_4\beta_1$ binding moiety, a biotin moiety, and a maleimide moiety.

An integrin-binding moiety (LLP2A-biotin-maleimide, as shown in FIG. 4) was incubated with Fc-Sec-His and Fc-Stop as described above. The moiety was prepared using protocols as provided in Song et al., *Bioorg. Med. Chem. Lett.*, 14: 161-165 (2004), and Peng et al., *Nat. Chem. Biol.*, 2: 381-389 (2006). Binding to HEK 293F cells, which express human integrin $\alpha_4\beta_1$, was analyzed by flow cytometry using 10 micrograms/mL of treated Fc-Sec-His, Fc-stop as a negative control, and the integrin binding moiety alone as a positive control.

Figure 5:
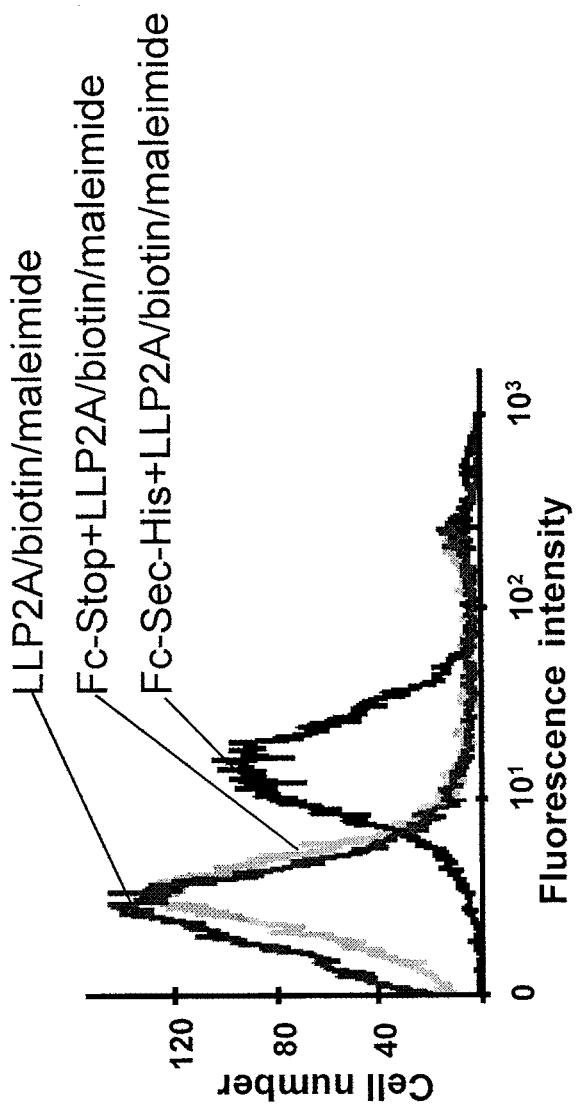
FIG. 5 is a flow cytometry plot of the Fc-Sec-His protein after incubation with HEK 293F cells expressing the integrin binding moiety, as compared to the Fc-stop protein or the integrin binding moiety alone.

As shown in FIG. 5, Fc-Sec-His bound strongly to the integrin-expressing cells, but Fc-stop did not. These results confirm that the integrin binding property of the moiety can be conferred on the hybrid molecule.

EXAMPLE 5

This example demonstrates in a clinical context that binding activity of a synthetic small molecule is maintained when the synthetic small molecule is bound to an antibody molecule.

Peripheral Blood Mononuclear Cells (PBMC) from untreated B-CLL patients were either freshly prepared or thawed up immediately before use. After 1 h incubation in 10% (v/v) FCS/PBS, cells were centrifuged, resuspended in 1% (v/v) FCS/PBS and aliquots of 50 μL containing $5\times10^5$ cells were distributed into a V-bottom 96-well plate (Corning). Fc-LLP2A-derived proteins (prepared as in Example 4) as well as biotinylated mouse anti-human Integrin α4 antibody were added to the cells at 5 μg/mL final concentration and incubated for 1 h. Subsequently, the cells were washed twice with 1% (v/v) FCS/PBS and incubated for 1 h with a 1:25 dilution of PE-conjugated streptavidin (BD Biosciences) in 1% (v/v) FCS/PBS. After two washing steps, the cells were resuspended in 400 μL in 1% (v/v) FCS/PBS and analyzed using a FACScan instrument (Becton-Dickinson). All steps were carried out on ice.

Figure 6:
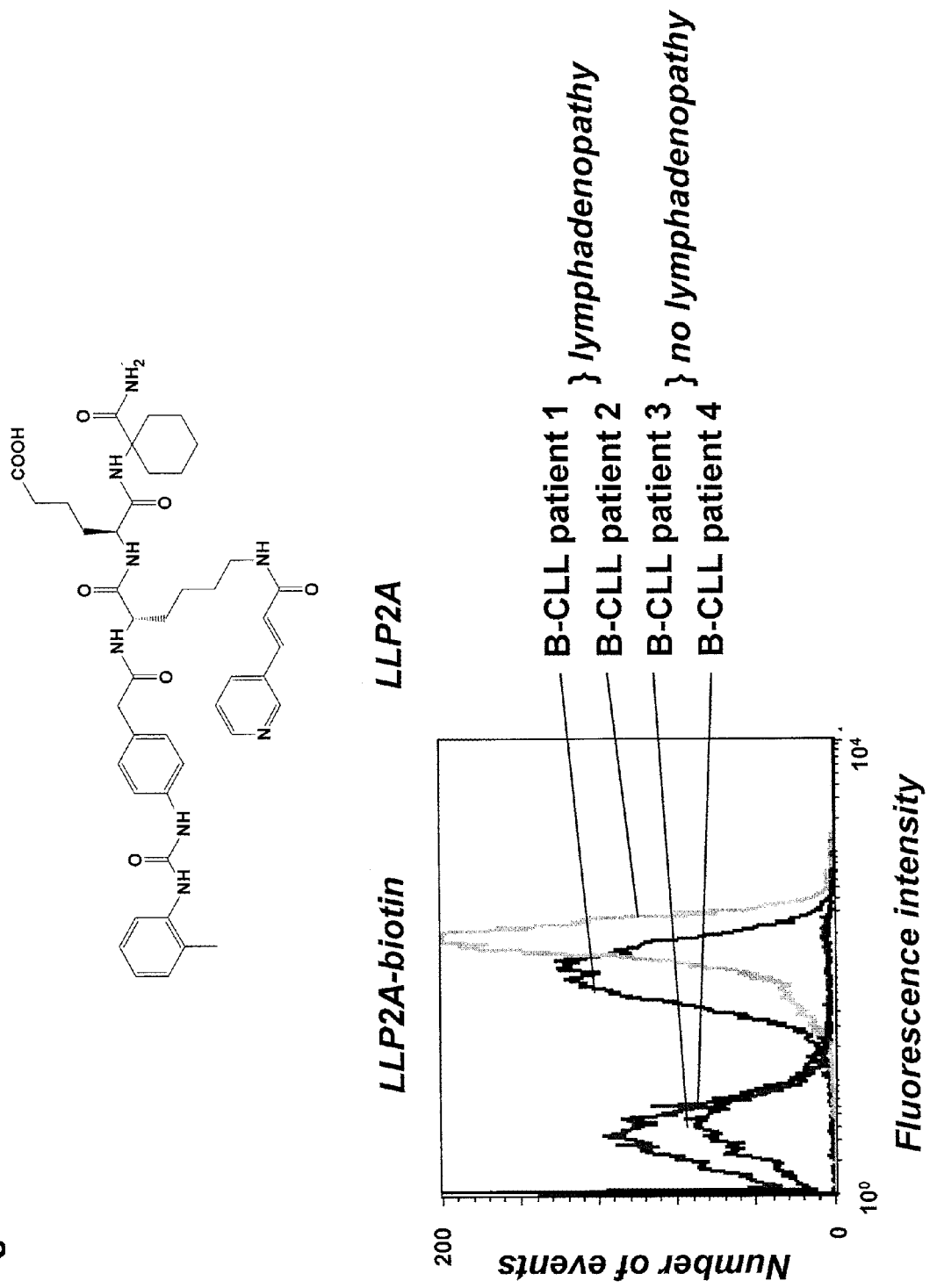
FIG. 6 is a flow cytometry plot of LLP2A-biotin after incubation with primary human chronic lymphocytic leukemia (CLL) cells from two patients with lymphadenopathy and two patients without lymphadenopathy.
Figure 7:
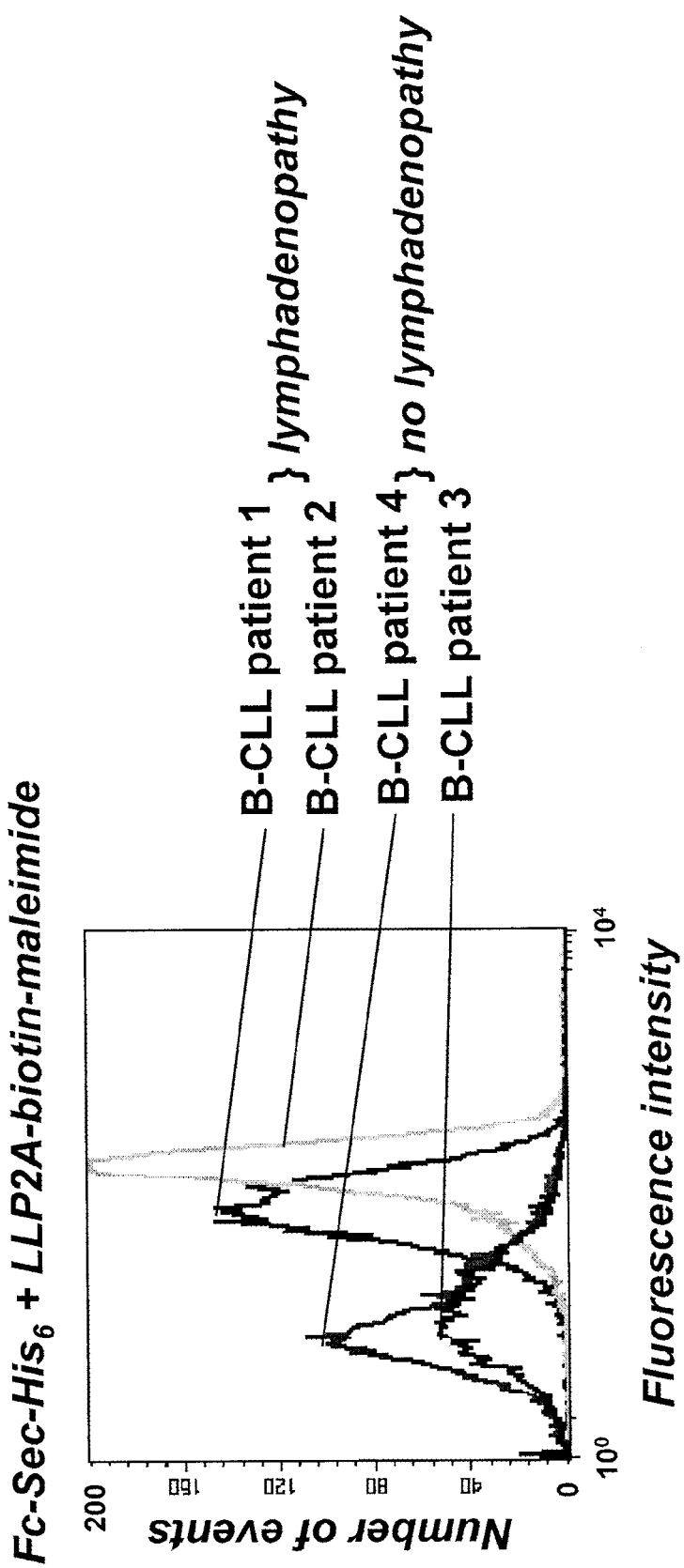
FIG. 7 is a flow cytometry plot of Fc-Sec-His conjugated to LLP2A-biotin-maleimide after incubation with primary human CLL cells from two patients with lymphadenopathy and two patients without lymphadenopathy.

When compared to a control profile of known integrin binding moiety LLP2A-biotin (FIG. 6), flow cytometry of Fc-Sec-His conjugated to the LLPA-biotin-maleimide integrin binding moiety (shown in FIG. 4) indicates similar patterns of binding to integrin receptors in patients having increased receptor expression versus patients not having increased receptor expression (FIG. 7).

These results show that an antibody conjugated to a synthetic molecule can be employed in a clinical context with similar effect to the un-conjugated synthetic molecule alone.

EXAMPLE 6

This example demonstrates that the serum half-life of a synthetic small molecule bound to an antibody molecule in vivo is greater than the serum half-life of the synthetic small molecule alone in vivo.

Each mouse received a single 100-μL tail vein injection of 10 mg/mL (200 μM) of the Fc-Sec-His/LLP2A-biotin in PBS (group 1) or 360 μg/mL (200 μM) free LLP2A-biotin in DMSO (group 2) on day 1. Thirty minutes after the tail vein injection one retro-orbital blood draw of approximately 50 μL from each mouse was taken. This blood draw was repeated after 24, 48, 72, and 96 hours for each mouse. Serum of each blood draw was isolated, 10× diluted, and incubated with Raji cells. Binding of Fc-LLP2A and LLP2A to the cells was detected as described in Example 5.

Whereas free LLP2A-biotin was undetectable 24 hours after injection, Fc-Sec-His/LLP2A-biotin was still present after 4 days.

These results demonstrate that that the circulatory half-life of a synthetic small molecule bound to an antibody molecule is increased compared to the synthetic small molecule alone.

EXAMPLE 7

This example demonstrates that in vitro activity is retained for an antibody bound to a small molecule.

LLP2A was previously shown to interfere with the interaction of integrin $\alpha_4\beta_1$ and VCAM-1 (Peng et al., *Nat. Chem. Biol.*, 2: 381-389 (2006)). A cell adhesion assay was performed to determine whether Fc-Sec-His/LLP2A-biotin and free LLP2A-biotin similarly interfered with the $\alpha_4\beta_1$ and VCAM-1 interaction. A 96-well Costar 3690 plate (Corning) was coated with 1 μg recombinant human VCAM-1 (R&D Systems) in 25 μL PBS and blocked with 3% (w/v) BSA/PBS. Raji cells ($1\times10^5$ cells in 50 μL PBS) were incubated with 10 μg/ml Fc-Sec-His/LLP2A-biotin, a mouse anti-human integrin $\alpha_4\beta_1$ mAb (R&D Systems), or an equimolar concentration of free LLP2A-biotin, and added to the prepared plate. Non-adherent cells were removed by washing twice with PBS. Adherent cells were subsequently detached by vigorous pipetting, and their number was determined by flow cytometry using AccuCount blank particles (Spherotech) for normalization. All incubations were for 1 hour at 37° C.

Figure 8:
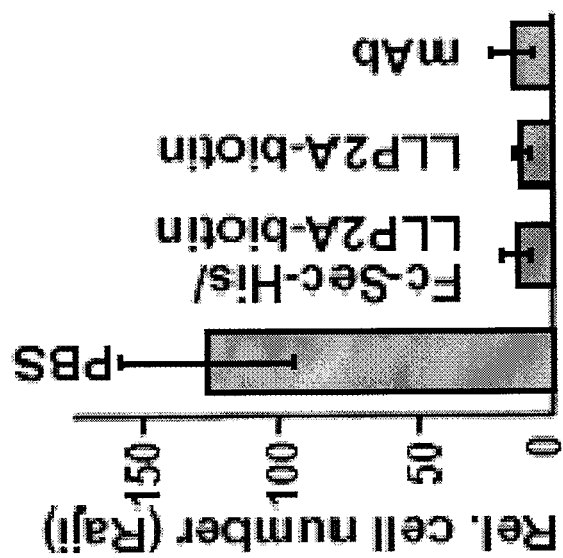
FIG. 8 depicts the relative number of cells adhering to coated VCAM-1, as determined by flow cytometry. Shown are mean±SD of triplicates.

Fc-Sec-His/LLP2A-biotin and free LLP2A-biotin were found to block the binding of Raji cells to immobilized human VCAM-1 as potently as a mouse anti-human integrin $\alpha_4\beta_1$ mAb (FIG. 8). When tested over a concentration range from 0.02 to 200 nM, Fc-Sec-His/LLP2A-biotin was found to be as potent as free LLP2A-biotin (data not shown). Therefore, conjugation to the generic Fc protein did not weaken the pharmacological activity. Similar results (data not shown)

were obtained for the binding of Raji cells to TNFα-activated human umbilical vein endothelial cells.

This study shows that an antibody conjugated to a synthetic molecule can maintain the biological activity of the synthetic molecule.

EXAMPLE 8

This example demonstrates the use of generic Fc protein conjugated to a small synthetic molecule for exploitation of FcRn binding.

Soluble human FcRn consisting of α-chain and β2 microglobulin was designed, expressed, and purified based on the previously reported generation and crystallization of soluble rat FcRn (Gastinel, *Proc. Natl. Acad. Sci. USA*, 89: 638-642 (1992)). Using the mammalian expression vector PIGG as described in Rader et al., *FASEB J.*, 16: 200-2002 (2002), α-chain and β2 microglobulin of heterodimeric human FcRn were expressed by an engineered bidirectional CMV promoter cassette. A PCR fragment encoding human β2 microglobulin was amplified from a full-length cDNA plasmid (OriGene) by PCR using primers beta-5' and beta-3' and cloned into PIGG by SacI/SalI ligation. A PCR fragment encoding the extracellular part of the human FcRn α-chain (nucleotides 70-1095) was amplified from a full-length cDNA plasmid (OriGene) by overlap extension PCR using primer pairs alpha-5'/HindIII-mut3' and HindIII-mut5'/alpha-3' and cloned into PIGG by HindIII/XbaI ligation. Both expression cassettes were verified by DNA sequencing.

Transient transfection of the soluble human FcRn expression vector into HEK 293F cells, culturing of the cells, and concentration of the supernatant was carried out as described above for Fc protein expression. The concentrated supernatant was subsequently brought into acidic PBS (pH 6.0). For purification, Fc-stop protein was immobilized to an NHS HiTrap column (GE Healthcare) using the manufacturer's protocol. After loading the concentrated supernatant in acidic PBS (pH 6.0), the column was washed with 30 mL acidic PBS (pH 6.0), and bound soluble human FcRn was eluted with neutral PBS (pH 7.4). Purified soluble human FcRn (5 μg) was analyzed by electrophoresis on a NuPage 4-12% gradient gel (Invitrogen) followed by staining with SimplyBlue SafeStain (Invitrogen). The binding of Fc-Sec-His/LLP2A-biotin and Fc*-Sec-His/LLP2A-biotin to soluble human FcRn was analyzed by ELISA. All steps were carried out side-by-side in acidic PBS (pH 6.0) or neutral PBS (pH 7.4) for 1 h at 37° C. First, 500 ng of soluble human FcRn in 25 μL PBS was coated on a 96-well Costar 3690 plate (Corning). After blocking with 3% (w/v) BSA/PBS, the plate was incubated with Fc-Sec-His/LLP2A-biotin or Fc*-Sec-His/LLP2A-biotin at 4 μg/mL (200 ng/well) followed by washing with acidic or neutral PBS (10×200 μL/well) and incubation with HRP-coupled streptavidin (50 ng/well) in 1% (w/v) BSA/PBS. The plate was washed with acidic or neutral PBS as before, and colorimetric detection was performed using 2,2'-azino-bis(3-ethylbenzthiazoline)-6-sulfonic acid (Roche) as substrate according to the manufacturer's directions.

Fc-Sec-His/LLP2A-biotin and Fc*-Sec-His/LLP2A-biotin were then analyzed by ELISA for binding to purified human FcRn at pH 6.0 and at pH 7.4. Both Fc conjugates were found to bind to FcRn at pH 6.0, but not at pH 7.4. Thus, these results demonstrate that the Fc conjugates have the same characteristic and physiologically relevant pH-dependent interaction with FcRn through which both IgG recycling and transcytosis have previously been shown to be mediated (Roopenian et al., *Nat. Rev. Immunol.*, 7: 715-725 (2007)).

EXAMPLE 9

This example demonstrates a physiologically relevant interaction of Fc-Sec-His/LLP2A-biotin with FcRn in vivo.

Transcytosis capacity of the Fc-Sec-His/LLP2A-biotin conjugate was evaluated in the neonatal intestine model as described in Roopenian et al., *Nat. Rev. Immunol.*, 7: 715-725 (2007)). For this evaluation, 0.5 mg of Fc-stop, Fc-Sec-His/LLP2A-biotin, and Fc-Sec-His conjugated to commercially available biotin-iodoacetamide, as well as an equimolar amount of free LLP2A-biotin, were administered intragastrically to 10-day old mice. Sera prepared after 24 hours from cardiac puncture bleeds were analyzed by flow cytometry using Raji cells and by Western blotting.

Both mouse studies were carried out by Biocon (Rockville, Md.) in accordance with the Guide for the Care and Use of Laboratory Animals published by the National Institutes of Health. Blood clearance. Two groups of three C57BL/6 mice each were injected i.v. (tail vein) with 100 μL of 10 mg/mL (200 μM) Fc-Sec-His/LLP2A-biotin in PBS or with 100 μL 360 μg/mL (200 μM) free LLP2A-biotin in DMSO. Sera from retro-orbital bleeds were prepared 30 min, 24 h, 48 h, 72 h, and 96 h after injection. Sera were tenfold diluted in 1% (v/v) FCS/PBS and analyzed by flow cytometry using Raji cells as described above. Transcytosis. Four groups of two 10-day old C57BL/6 mice each received Fc-stop, Fc-Sec-His/LLP2A-biotin, Fc-Sec-His/biotin, or free LLP2A-biotin; 0.5 mg protein or an equimolar amount of free LLP2A-biotin was combined with 80 μg soybean trypsin inhibitor in a total volume of 50 μL PBS and administered intragastrically using a 2.54 cm (1-inch) straight gavage needle with a 1.25-mm diameter ball. No toxicity was noted. After 24 h, the mice were anesthetized with ketamine xylazine anesthesia cocktail and bled out via cardiac puncture. Sera were tenfold diluted in 1% (v/v) FCS/PBS and analyzed by flow cytometry using Raji cells as described above.

These analyses revealed that transcytosis of Fc-Sec-His/LLP2A-biotin was highly efficient (FIG. 9B). Western blotting across timepoints of 30 minutes, 24 hours, 48 hours, 72 hours, and 96 hours confirmed the blood clearance of Fc-Sec-His/LLP2A-biotin following reducing SDS-PAGE. In addition, transcytosis of Fc-Sec-His/LLP2A-biotin was as efficient as transcytosis of Fc-stop and Fc-Sec-His/biotin.

With its preserved ability to enter the blood stream through FcRn-mediated transcytosis, the generic Fc protein provides a vehicle for alternative administration routes of small synthetic molecules across epithelial or endothelial cell barriers. For example, the expression of FcRn in human upper airway epithelial cells mediates the transport of aerosolized IgG and Fc fusion proteins from the lung to the blood with an efficacy as high as i.v. injection (Roopenian et al., *Nat. Rev. Immunol.*, 7: 715-725 (2007); Spiekermann et al., *J. Exp. Med.*, 196: 303-310 (2002)).

The results of this study demonstrate that the Fc conjugates are capable of entering the bloodstream via transcytosis, and that certain in vivo administration methods, such as a model for inhaled aerosols, can be used in the antibody-small molecule conjugate.

EXAMPLE 10

This example demonstrates the preparation and use of an IgG-Sec conjugate using the commercially available CD20 antibody Rituximab (RITUXAN®).

PIGG-Rituximab-Sec-His.

The sequences of the variable domains VL and VH of Rituximab were obtained from Anderson et al., U.S. Pat. No. 5,736,137. DNA sequences optimized for human cell expression were custom synthesized (GenScript) and cloned by XbaI/HindII (VL) and ApaI/SacI (VH) into the previously described bidirectional Vector PIGG. In this vector, heavy and light chains are expressed by an engineered bidirectional CMV promoter cassette. For the expression of a C-terminal selenocysteine in the heavy chain, a SacII/SalI fragment of the previously described pCEP4-Fc-Sec-His was cloned into PIGG-Rituximab by SacII/SalI ligation. This fragment consisted of the end of $CH_3$, a TGA codon, followed by six His codons, a TAA codon, an engineered SalI site, and a portion of the 3'-UTR of the thioredoxin reductase 1 gene containing the SECIS element for recoding of the TGA stop codon to selenocysteine insertion. The resulting plasmid was named PIGG-Rituximab-Sec-His. See FIGS. 10A-B.

PIGG-Rituxi-Fab-Sec-His.

For the generation of a plasmid expressing Rituxi-Fab-Sec-His (FIG. 10C), an ApaI/SalI fragment of PIGG-Rituximab-Sec-His was replaced by a fragment expressing the $C_H1$ portion downstream of the ApaI site, followed by a TGA codon, six His codons, a TAA codon, and the SECIS element-containing 3'UTR portion as described above. This new fragment was generated by PCR using PIGG-Rituximab-Sec-His as a template. Using primer pairs (a) IX-5'(ccaagggcccatcggtcttc-ccctggcaccctcctccaagagcacctctgggggca) (SEQ ID NO:14) and IX-3' (atgtcatgtgtgagttttgtcacaagatttgggctcaactttctt) (SEQ ID NO:15), (b) X-5' (tcttgtgacaaaactcacacatgacat-caccatcaccatcactaagcccccagtgtggatgctgttgcca) (SEQ ID NO:16) and X-3' (ctaggtcgactttatttgccaaatgagatgaggacgtgag) (SEQ ID NO:17), two PCR fragments amplified with these two primer pairs were fused by overlap extension PCR and cloned by ApaI/SalI ligation.

The mammalian expression vectors described above were transiently transfected into HEK 293F cells (Invitrogen) with 293fectin (Invitrogen) using conditions detailed in the manufacturer's protocol. Transfected HEK 293F cells were cultured in FreeStyle serum-free medium (Invitrogen), supplemented with 1 µM $Na_2SeO_3$ (Sigma), in spin flasks (Integra Biosciences) under constant rotation at 75 rpm in a humidified atmosphere containing 8% $CO_2$ at 37° C. Three days after transfection, the medium was collected after centrifugation, replaced for two additional days, and collected again. This procedure was repeated once for two additional days. The combined supernatants were filtered through a 0.45-µm membrane and tenfold concentrated using an ultrafiltration device with a 10-kDa cutoff membrane (Millipore). While the concentrate containing Rituximab-Sec-His was loaded on a 1-mL recombinant Protein G HiTrap column (GE Healthcare), Rituxi-Fab-Sec-His was purified using a 1-mL NHS-activated HiTrap column coated with goat anti-human Fab polyclonal IgG (Bethyl Laboratories). PBS was used for column equilibration and washing, 0.5 M acetic acid (pH 3.0) for elution, and 1 M Tris-HCl (pH 8.0) for immediate neutralization. The neutralized eluate was dialyzed at 4° C. overnight against PBS using Slide-A-Lyzer cassettes with 10-kDa cutoff (Pierce) and concentrated with 10-kDa cutoff centrifugal filter devices (Millipore). In order to separate Rituxi-Ig proteins with inserted selenocysteine (Rituxi-Ig-Sec-His) from those without (Rituxi-Ig-stop), the purified Ig proteins were tenfold diluted in loading/washing buffer (500 mM NaCl and 25 mM imidazol in PBS) and loaded on a 1-mL IMAC column (HisTrap; GE Healthcare). The flow-through of the column containing Rituxi-Ig-stop was collected. Subsequently, the column was washed with 50 mL loading/washing buffer, and the bound Rituxi-Ig-Sec-His proteins were eluted with elution buffer (500 mM NaCl and 500 mM imidazol in PBS). Both eluate and flow-through were dialyzed and concentrated as before.

For selective conjugation at the Sec interface, Rituxi-Ig-Sec-His and Rituxi-Fab-Sec-His proteins and negative controls (Rituxi-Ig-stop and Rituxi-Fab-stop) were diluted in 15 mL 100 mM sodium acetate (pH 5.2) and concentrated to 4 µM using a 10-kDa cutoff centrifugal filter device. DTT at 0.1 mM followed by either fluorescein-5-maleimide, maleimide-$PEO_2$-biotin (both from Pierce), or 7.5 kDa biotin-poly(ethyleneglycol)-maleimide (biotin-peg-maleimide; JenKem Technology) at 10 µM final concentration were added to the protein and incubated for 50 min at room temperature in the dark. The conjugated proteins were subsequently diluted in 15 mL 100 mM sodium acetate (pH 5.2) and concentrated to 250 µL as described above. This step was repeated once with 15 mL 100 mM sodium acetate (pH 5.2) and subsequently twice with 15 mL PBS to remove unconjugated compounds. Both proteins were selectively biotinylated. Proteins without Sec remained unbiotinylated. ELISAs prepared on coated Rituximab-Sec-His and Rituxi-Fab-Sec-His detected biotin with HRP-coupled streptavidin and with HRP-coupled donkey anti-human IgG polyclonal antibodies. Commercial Rituximab (RITUXAN®) served as a control. After selective biotinylation at the Sec interface, the correct assembly of both Ig chains of Rituxi-Fab-Sec/biotin was confirmed by non-reducing SDS-PAGE and Coomassie staining Untreated Rituxi-Fab-Sec-His and Rituxi-Fab-stop served as controls.

Selective conjugation of Rituximab-Sec-His and Rituxi-Fab-Sec-His preserved the correct assembly the protein chains. Following selective biotinylation, 5 µg of Rituximab-Sec-His/biotin and Rituximab-stop were analyzed by non-reducing SDS-PAGE followed by Coomassie staining Rituximab served as a control. The correct size of the protein and comparison with Rituximab indicated that neither selective modification at the Sec interface (Rituximab-Sec-His/biotin) nor incubation in the conjugation buffer (Ritxmab-stop) affects the tetrameric structure of the protein.

Soluble human FcRn was engineered and expressed as described above. Briefly, both cDNA sequences of the heterodimeric human FcRn, α-chain and β2 microglobulin, were cloned into the bidirectional CMV promoter cassette of the PIGG vector. Transient transfection of the soluble human FcRn expression vector into HEK 293F cells, culturing of the cells, and concentration of the supernatant were carried out as described for Rituximab expression. The concentrated supernatant was subsequently brought into acidic PBS (pH 6.0). For purification, Fc-stop protein was immobilized to an NHS HiTrap column (GE Healthcare) using the manufacturer's protocol. After loading the concentrated supernatant in acidic PBS (pH 6.0), the column was washed with 30 mL acidic PBS (pH 6.0), and bound soluble human FcRn was eluted with neutral PBS (pH 7.4).

Analysis of selective conjugation. To confirm selective biotinylation at the Sec interface through (+)-biotinyl-iodoacetamidyl-3,6-dioxaoctanediamine, wells of a 96-well Costar 3690 plate (Corning) were incubated with 200 ng Rituximab-Sec-His/biotin, Rituximab-stop, Rituxi-Fab-Sec-His-biotin, Fab-stop, or Rituximab in 25 µL PBS. After blocking with 3% (w/v) BSA/PBS, the plate was incubated with either HRP-coupled streptavidin (50 ng/well) or a 1:1,000 dilution of HRP-coupled donkey anti-human IgG polyclonal antibodies (Jackson ImmunoResearch Laboratories) in 1% (w/v) BSA/PBS. After washing with water (10×200 µL/well), colorimetric detection was performed using 2,2'-azino-bis(3-ethylbenzthiazoline)-6-sulfonic acid (Roche) as substrate according to the manufacturer's directions.

Analysis of Fc Receptor Binding.

To analyze and compare the binding of Rituximab and specifically conjugated Rituximab-Sec-His to commercially available soluble human FcγRI, FcγRIIA, and FcγRIIIA (all from R&D Systems) as well as to soluble human FcRn, 500 ng of each Fc receptor was coated and blocked on a 96-well plate as described above. The plate was then incubated with Rituximab, Rituximab-Sec-His/biotin, and Rituximab-Sec-His/fluorescein for FcRn binding at 8 µg/mL (400 ng/well) followed by washing with $H_2O$, incubation with HRP-coupled streptavidin (50 ng/well) or HRP-coupled donkey anti-human IgG polyclonal antibodies (1:1000) in 1% (w/v) BSA/PBS, and colorimetric detection as described in Example 8 above. For multimeric binding of Rituximab-Sec-His/biotin, 1 µg of the Fc conjugates was pre-incubated with 250 ng HRP-coupled streptavidin followed by incubation with coated and blocked FcγRIIA, washing with $H_2O$, and colorimetric detection. For binding of Rituximab, Rituximab-Sec-His/biotin, and Rituximab-Sec-His/fluorescein to FcRn, all steps were carried out side-by-side in acidic PBS (pH 6.0) or neutral PBS (pH 7.4). Binding for both Rituximab conjugates was detectable at pH 6.0, but not at pH 7.4. Rituximab was used as a positive control.

For detecting multimeric IgG binding in the Fcγ receptor binding assay, 1 µg of rituximab-based IgG-Sec-His/biotin and Rituxan® (negative control) were pre-incubated with 250 ng HRPcoupled streptavidin followed by incubation with coated and blocked FcγRIIA and FcγRIIIA, washing, and colorimetric detection. All incubations were for 1 hour at 37° C.

Flow cytometry assays were conducted on the resulting conjugates. Human Burkitt's lymphoma cell line Raji was purchased from ATCC. All incubations were for 1 hour on ice. Cells were centrifuged and resuspended in 1% (v/v) FCS/PBS, and aliquots of 50 µL containing $5 \times 10^5$ cells were distributed into a V-bottom 96-well plate (Corning). The cells were then incubated with Rituximab, Rituximab-Sec-His/biotin, a Rituximab-Sec-His/fluorescein, Rituximab-stop, Rituxi-Fab-Sec-His/biotin, and CAMPATH® along with other corresponding negative controls (all 0.6 µM). After washing twice with 1% (v/v) FCS/PBS, the cells were incubated with a 1:25 dilution of PE-coupled streptavidin (BD Biosciences) or with FITC-coupled goat anti-human Fab polyclonal (Fab')$_2$ fragments (Jackson ImmunoResearch Laboratories). This step was skipped for cells that had been incubated with Rituximab-Sec-His/fluorescein. After washing twice as before, the cells were resuspended in 400 µL 1% (v/v) FCS/PBS and analyzed using a FACScan instrument (Becton-Dickinson). For the competition experiment, the cells were first incubated with the anti-CD52 monoclonal antibody CAMPATH® or Rituxan (all 0.6 µM). For detection, a 1:25 dilution of PE-coupled streptavidin (BD Biosciences) was used.

Rituximab-Sec-His/biotin and Rituximab bound to Raji cells with equal affinities, indicating that Sec-mediated conjugation does not impair binding characteristics. In contrast, due to the monovalent binding of Rituxi-Fab-Sec-His/biotin, binding intensity is slightly reduced (FIG. 11A). The specific binding of Rituximab-Sec-His/biotin can compete with Rituximab. While pre-incubation with the anti CD52 monoclonal antibody CAMPATH® did not affect binding of Rituximab-Sec-His/biotin, pre-incubation with commercial Rituximab (RITUXAN®) strongly reduced Rituximab-Sec-His/biotin binding (FIG. 11B), demonstrating the high specificity of Sec-modified Rituximab.

Rituximab-Sec-His and Rituximab-stop were exposed to a FITC derivative with an electrophilic maleimide moiety followed by incubation with Raji cells. While incubation of Raji cells with Rituximab-Sec-His/FITC resulted in a clear and homogenous signal, exposure with FITC-treated Rituximab-stop reached only basal levels like the corresponding unconjugated proteins and Strep-PE alone (FIG. 11C). Sec-mediated conjugation with FITC was therefore found to be highly efficient and selective.

Following selective biotinylation at the Sec interface, Rituximab-Sec-His/biotin was analyzed for binding to immobilized recombinant FcγRI, FcγRIIA, and FcγRIIIA with HRP-coupled streptavidin and HRP-conjugated goat anti-human Fab polyclonal F(ab')$_2$ fragments. Rituximab was used as a positive control. The avidity of Rituximab-Sec-His/biotin to FcγRIIA strongly increased after pre-incubation with HRP-coupled streptavidin for multimerization. FcRn receptor binding of Rituximab-Sec His/biotin and Rituximab-Sec His/fluorescin were evaluated using ELISA as above. Rituximab-Sec His/biotin and Rituximab-Sec His/fluorescin were analyzed for binding to immobilized recombinant human FcRn with HRP-coupled streptavidin.

To determine whether Sec-conjugation had any effect on the cytotoxic effects of Rituximab, Raji cells were centrifuged and resuspended in 1% (v/v) FCS/PBS, and aliquots of 50 µL containing $5 \times 10^5$ cells were distributed into a V-bottom 96-well plate (Corning). After incubation with Rituximab, Rituxi-Sec-His/fluorescein, or Rituxi-Fab-Sec-His/biotin (0.6 µM) for 1 hour on ice, cells were washed twice and incubated with 10% rabbit complement of 3-4 weeks old rabbits (Pel-Freez) for 2 hours at 37° C. After the addition of 100 µg/ml propidium iodide (PI), dead cells were detected by PI accumulation using a FACScan instrument (Becton-Dickinson). Rituxi-Sec-His/fluorescein was as potent as Rituximab in mediating CDC. Rituximab served as a positive control, and Rituxi-Fab-sec-His was used as a negative control, and was found to be incapable of mediating CDC. In contrast to the strong cytotoxic effect of Rituximab in combination with the rabbit serum, neither the antibody nor rabbit serum alone mediated complement-dependent cytotoxicity (FIG. 12A). Incubation of Raji cells with Rituximab-Sec-His specifically conjugated with FITC (FIG. 12B) or Geldanamycin (GA) (FIG. 12C) indicated equal cytotoxicity when co-incubated with rabbit serum, indicating that Sec-specific conjugation of Rituximab-Sec-His does not affect the ability to mediate complement-dependent cytotoxicity.

The results of this study demonstrate that Rituximab-Sec-His/biotin interacts with Fcγ receptors in a pH dependent manner but that Sec conjugation has no effect on complement dependent cytotoxicity.

EXAMPLE 11

This example demonstrates that a mixture of proteins with and without C-terminal selenocysteine can be separated following selective biotinylation.

A mammalian expression vector was cloned that was identical to PIGG-rituximab-Sec-His but without the (His)6-encoding sequence. To express rituximab with a C-terminal Sec but without a His tag, mammalian expression vector pCEP4-Fc-Sec was prepared using the same methods used to construct pCEP4-Fc-Sec-His as described in Example 1. Using pCEP4-Fc-Sec-His as template, a PCR fragment was amplified with primer pair VIII-5' (gcctaagcttgtctccgggtgcctgataagccccagtgtggatgctgttg) (SEQ ID NO:19) and VIII-3'

(agctctcgaggccaaatgagatgaggacgtgag) (SEQ ID NO:20) and cloned into pCEP4-Fc by HindIII/XhoI ligation. The resulting plasmid was designated pCEP4-Fc-Sec. An Fc-Sec encoding portion of pCEP4-Fc-Sec was subsequently transferred into PIGG-rituximab by SacII/SalI ligation, resulting in PIGG-rituximab-Sec.

A mixture of IgG-Sec and IgG-stop protein was purified from supernatants of transiently transfected HEK 293F cells by Protein G affinity chromatography. The purified mixture of Rituxi-Sec (without His tag) and IgG-stop was subjected to selective conjugation to biotinmaleimide followed by monomeric avidin affinity chromatography. Subsequent analysis by Western blotting revealed efficient separation of IgG-Sec/biotin (eluate) and IgG-stop (flow-through). This analysis also confirmed selective conjugation at the Sec interface as reflected by a biotinylated heavy chain and a non-biotinylated light chain band.

Further analysis by flow cytometry using PE-coupled streptavidin showed that purified Rituxi-Sec/biotin binds to Raji cells as efficiently as Rituxi-Sec-His/biotin (FIG. 15).

These results demonstrate that a His tag is convenient but not necessary for separating mixtures of proteins with and without C-terminal Sec as long as the conjugated compound contains a handle for protein purification.

EXAMPLE 12

This example demonstrates the preparation of a pegylated Rituxi-Fab-Sec-His conjugate as well as effects of this pegylation on serum concentration levels by administration of Rituxi-Fab-Sec-His/PEG-biotin in a mouse model.

Using the selective conjugation conditions described in Example 10, purified Rituxi-Fab-Sec-His was reacted with a commercially available 7.5-kDa biotin-PEG-maleimide compound. Size-exclusion chromatography following selective conjugation resulted in the separation of two protein fractions, indicated by peak 1 and peak 2 in a ratio of approximately 2:1 (FIG. 16A). By contrast, rituximab-based Fab-stop, subjected to same conjugation conditions in the presence of biotin-PEG-maleimide, only revealed peak 2 (FIG. 16A). Flow cytometry using the concomitantly conjugated biotin group for detection confirmed that peak 1 contained the rituximab-based Fab-Sec-His/PEG-biotin fraction and peak 2 contained the unconjugated Fab fraction. As shown in FIG. 16B, peak 1, but not peak 2, revealed strong binding to Raji cells. As previously observed for rituximab-based Fab-Sec-His/biotin and attributed to lower avidity (FIG. 11A), the binding of Fab-Sec-His/PEG-biotin was found to be somewhat weaker than the binding of IgG-Sec-His/biotin. The remaining weak binding activity in peak 2, which was slightly above the background defined by negative control conjugate Fc-Sec-His/PEG-biotin (FIG. 5B), can be explained by an incomplete separation of peak 1 and peak 2. The presence of Rituxi-Fab in both peak 1 and peak 2 was confirmed by flow cytometry (FIG. 16B) and Western blotting, using donkey anti-human Fab polyclonal antibodies for detection.

In vivo tests in a mouse model were then conducted to investigate whether PEGylation extended the circulatory half-life of the Fab molecule.

The mouse study was carried out by Biocon, Inc. (Rockville, Md.) in accordance with the *Guide for the Care and Use of Laboratory Animals* published by the National Institutes of Health. Each of three groups of three adult C57BL/6 mice was injected i.v. (tail vein) with 100 µL of 3 mg/mL Fab-Sec-His/PEG-biotin, Fab-stop, or Rituximab (RITUXAN®) in PBS. Sera from retro-orbital bleeds were prepared 30 min, 24 h, 48 h, 72 h, and 96 h after injection. Sera were diluted ten-fold in 1% (v/v) FCS/PBS and analyzed by flow cytometry using Raji cells and Cy5-coupled goat anti-human F(ab')2 polyclonal antibodies (Jackson ImmunoResearch) or PE-coupled streptavidin as described in Example 10 (FIG. 16C).

Consistent with a previously reported half-life of 199 h for human IgG1 in SCID mice (Zuckier et al., *Cancer Res.*, 58: 3905-08 (1998)), Rituximab (RITUXAN®) revealed only marginal weakening over the course of the experiment. Although the signals obtained for both Fab preparations indicated much shorter circulatory half-lives, the 7.5-kDa PEG group was found to delay the clearance of the Fab molecule, rendering it detectable 24 h after intravenous injection (FIG. 16C). The retained Fab-Sec-His/PEG-biotin conjugate was detectable with both donkey anti-human Fab polyclonal antibodies (FIG. 16C) and streptavidin, confirming the previously noted stability of C-terminal Sec conjugates in vivo.

These results demonstrate that the PEGylated Rituxi-Sec-Fab had an extended circulatory half-life compared to the unconjuaged Rituxi-Sec-Fab.

EXAMPLE 13

This example demonstrates the use of a flexible trifunctional poly(ethylene glycol)-succinamide-Lysine-Lysine-maleimide (PEG-SU-Lys-Lys-mal) linker to prepare an Fc-Sec-LLP2A antibody-drug conjugate as shown in FIG. 13.

Using solid-phase synthesis techniques as described in Thomas et al., *Bioorg. Medicinal Chem. Letters*, 18: 5785-88 (2008), the PEG-SU-Lys-Lys-mal linker was used to couple LLP2A to Fc-Sec. A biotin reporter molecule was employed as described in Example 2 to allow detection of Fc covalent adducts by avidin pull-down experiments followed by ELISA visualization. The Fc-Sec-LLP2A conjugate was then incupated with integrin $\alpha_4\beta_1$-expressing cells. The cells were washed and then treated with Cy5-labeled rabbit anti-human IgG. Under these conditions, cells only fluoresced if both the Fc and LLP2A components of the hybrid construct were present.

Competition experiments with an anti-integrin $\alpha_4$ mAb (purchased from Serotec) indicated that the Fc-Sec-LLP2A conjugate and the anti-integrin $\alpha_4$ mAb exhibited identical/overalapping epitopes as evidenced by the diminished binding of the Fc-Sec-LLP2A conjugate to lymphoma cells in the presence of the anti-integrin $\alpha_4$ mAb (FIG. 14).

These results demonstrate that the binding of the Fc-Sec-LLP2A conjugate to the cells is mediated by the peptidomimetic LLP2A and not by the Fc protein portion, and that the targeting specificity of the parent peptidomimetic for integrin $\alpha_4$ is retained in Fc-Sec-LLP2A conjugates using the PEG-SU-Lys-Lys-mal linker.

EXAMPLE 14

This example demonstrates that the synthetic molecule bound to a selenocysteine-antibody conjugate can be equipped with additional agents.

A maleimide derivative of folate was incubated with Fc-Sec-His and Fc-Stop as described in Examples 3-4. Binding to ovarian carcinoma cell line SKOV-3, which expresses folate receptor, was analyzed by flow cytometry using 10 micrograms/mL of treated Fc-Sec-His/folate-biotin, Fc-biotin as a negative control, and folate-biotin as a positive control. The results are depicted in the flow cytometry plot of FIG. 17.

As is apparent from the data reflected in FIG. 17, Fc-Sec-His/Folate-biotin bound strongly to the folate-receptor expressing cells, but Fc-biotin did not.

The folate was further equipped with an alkyne group using methods described in Thomas et al., Poster MEDI-409, 238th ACS National Meeting, Washington, D.C. (Aug. 16-20, 2009). Using azide-alkyne Huisgen cycloaddition ("click chemistry") under various reaction conditions, biotin-azide was added to the resulting Fc-Sec-His/folate-alkyne. The results of three reaction conditions are also depicted in the flow cytometry plot of FIG. 17.

As is apparent from the data reflected in FIG. 17, biotin-azide was successfully clicked onto Fc-Sec-His/folate-alkyne, and the conjugate retained its folate binding properties.

These results demonstrate that a selenocysteine-conjugated antibody can be modified to carry an alkyne functionality onto which azide derivatives of various compounds can be clicked.

EXAMPLE 15

This example demonstrates the preparation of a IgG-Sec conjugate using the anti-NKG2D monoclonal antibody KYK2.0, which is a fully human IgG. NKG2D is an activating receptor found on natural killer (NK) cells and a costimulatory receptor on certain T cells.

The KYK2.0-IgG, described in Kwong et al., *J. Mol. Biol.*, 384: 1143-56 (2008), was expressed as an IgG-Sec conjugate using the PIGG expression vector as described in Example 10. The resulting KYK2.0-Sec construct was incubated with LLP2A-biotin as described in Example 4. The correct assembly of KYK2.0-Sec/LLP2A-biotin was confirmed by non-reducing SDS-PAGE and Coomassie staining, ELISA, and Western Blotting.

Binding of the resulting conjugates was analyzed for KYK2.0-Sec/LLP2A-biotin using JeKo-1 cells. Flow cytometry of these conjugates as compared to LLP2A-biotin, a positive control, confirmed the potency of binding against $\alpha_4\beta_1$ expressing cells (KYK2.0-Sec/LLP2A-biotin) (FIG. 18).

EXAMPLE 16

This example demonstrates the preparation and use of an IgG-Sec/folate-biotin conjugate using the anti-NKG2D monoclonal antibody KYK2.0, as well as the cancer cell killing ability of such a conjugate.

The KYK2.0-IgG, described in Kwong et al., *J. Mol. Biol.*, 384: 1143-56 (2008), is expressed as an IgG-Sec conjugate using the PIGG expression vector as described in Example 10. The resulting KYK2.0-Sec construct is incubated with folate-biotin as described in Example 14. The correct assembly of KYK2.0-Sec/folate-biotin is confirmed by non-reducing SDS-PAGE and Coomassie staining, ELISA, and Western Blotting.

Binding of the resulting conjugates is analyzed for KYK2.0-Sec-His/folate-biotin using ovarian carcinoma cell line SKOV-3 as described in Example 14. Flow cytometry of these conjugates as compared to appropriate positive and negative controls confirms the potency of binding against folate-receptor expressing cells (KYK2.0-Sec-His/folate-biotin).

Cancer cell killing mediated by KYK-2.0 Fab (or IgG1)-Sec-His/LLP2A-biotin and KYK-2.0 Fab (or IgG1)-Sec-His/folate-biotin is determined by release of the intracellular enzyme lactase dehydrogenase (LDH) using effector and target cells prepared as follows.

Effector cells: PBMC are isolated from whole blood of healthy volunteers and stored at 37° C. overnight in RPMI 1640 plus 10% (v/v) fetal bovine serum (FBS), 20 mM Hepes (pH 7.4), and 100 U/mL human IL-2. Alternatively, human NK cells (CD16+ CD56+) are negatively selected and purified from human PBMC by magnetic activated cell sorting using the NK Cell Isolation Kit (Miltenyi Biotec) and expanded for 1 week in the presence of 10 ng/mL recombinant human IL-15 and artificial antigen presenting cells (see, e.g., Zhang et al., *J. Immunol.*, 179: 4910-8 (2007)) expressing human 4-1BBL and human IL-15Rα at a ratio of 1-2 to 1 (cell line 2D11).

Target Cells:

Human mantle cell lymphoma cell line Jeko-1 (which expresses integrin $\alpha_4\beta_1$) or human ovarian carcinoma cell line SKOV-3 (which were grown in folate-deficient medium for several weeks and express folate receptor FOLR1) are plated at $1\times10^5$ cells per well in a 96-well plate in (regular or folate-deficient) RPMI 1640 plus 5% (v/v) FBS and 15 mM Hepes (pH 7.4). The cells are incubated with 0.01 to 1 µg/mL KYK-2.0 Fab (or IgG1)-Sec-His/LLP2A-biotin and KYK-2.0 Fab (or IgG1)-Sec-His/folate-biotin, respectively, for 1 h at 37° C. Subsequently, the cells are washed to remove unbound conjugate.

Combining Effector and Target Cells:

The prepared target cells (T) are incubated with the prepared effector cells (E) in RPMI 1640 plus 5% (v/v) FBS and 15 mM Hepes (pH 7.4) for 4 h at 37° C. at E:T ratios of 1:1, 10:1, and 20:1. Target cell lysis is determined by release of LDH using the CytoTox 96 Non-Radioactive Cytotoxicity Assay kit (Promega) according to the manufacturer's protocol. The amount of LDH released is proportionate to target cell lysis. Samples are performed in triplicate and statistically analyzed.

The results are expected to show that the KYK2.0 conjugates can kill target cells by recruiting NKG2D-expressing effector cells.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A composition comprising (a) a hybrid molecule comprising a synthetic molecule and an antibody or antibody fragment selected from the group consisting of Fc, F(ab')2, Fab, scFv, IgGΔCH2, scFv2CH3, scFv4, scFv3, scFv2, dsFv, and scFv-Fc, wherein the antibody or antibody fragment comprises at least one selenocysteine residue, wherein the at least one selenocysteine residue is located within 10 amino acids of a C-terminus of the antibody or antibody fragment, wherein the at least one selenocysteine residue is cotranslationally incorporated at a UGA stop codon of the antibody or antibody fragment that was recoded from termination to selenocysteine insertion, and wherein the synthetic molecule is covalently linked to the antibody or antibody fragment at the at least one selenocysteine residue, and (b) a pharmaceutically acceptable carrier.

2. The composition of claim 1, wherein the antibody is selected from the group consisting of IgA, IgD, IgE, IgG, and IgM.

3. The composition of claim 1, wherein the antibody is rituximab.

4. The composition of claim 1, wherein the antibody fragment is an Fc domain.

5. The composition of claim 1, wherein the antibody fragment is an Fab domain.

6. The composition of claim 1, wherein the antibody or antibody fragment comprises only one selenocysteine residue.

7. The composition of claim 1, wherein the antibody or antibody fragment comprises more than one selenocysteine residue.

8. The composition of claim 1, wherein the at least one selenocysteine residue is located within 5 amino acids of the C-terminus of the antibody or antibody fragment.

9. The composition of claim 1, wherein the at least one selenocysteine residue is located at the C terminus of the antibody or antibody fragment.

10. The composition of claim 1, wherein the antibody or antibody fragment is produced using a eukaryotic expression system.

11. The composition of claim 10, wherein the antibody or antibody fragment is produced using a mammalian expression system.

12. The composition of claim 1, wherein the synthetic molecule comprises an iodoacetamide, bromoacetamide, chloroacetamide, maleimide, or acrylamide moiety.

13. The composition of claim 1, wherein the synthetic molecule comprises a binding moiety for an integrin selected from the group consisting of α4β1, α4β7, αvβ3, αvβ5, αVβ6, α5β1, and αIIBβ3.

14. The composition of claim 13, wherein the synthetic molecule comprises both an α4β1 and an α4β7 integrin binding moiety.

15. The composition of claim 1, wherein the synthetic molecule comprises a binding moiety for a receptor selected from the group consisting of CCR5, LHRH, CXCR4, TPO, folate, endothelin, and vitamin B12.

16. The composition of claim 1, wherein the synthetic molecule comprises a biotin moiety.

17. The composition of claim 1, wherein the synthetic molecule comprises an α4β1 integrin binding moiety, a biotin moiety, and a maleimide moiety.

18. The composition of claim 1, wherein the synthetic molecule comprises a radioisotope.

19. The composition of claim 1, wherein the synthetic molecule comprises a cytotoxic agent.

20. The composition of claim 19, wherein the cytotoxic agent is selected from the group consisting of doxorubicin, calicheamicin, maytansinoid, and auristatin.

21. The composition of claim 1, wherein the synthetic molecule is covalently linked to the selenocysteine residue by a polyethylene glycol (PEG) linker.

22. The composition of claim 21, wherein the PEG linker comprises poly(ethylene glycol)-succinamide-lysine-lysine-maleimide.

* * * * *

SEQUENCE LISTING

```
<160> NUMBER OF SEQ ID NOS: 20

<210> SEQ ID NO 1
<211> LENGTH: 94
<212> TYPE: DNA
<213> ORGANISM: Artificial Sequence
<220> FEATURE:
<223> OTHER INFORMATION: Synthetic Polynucleotide

<400> SEQUENCE: 1
gggtaccatg gactggacct ggaggatcct cttcttggtg gcagcagcca caggagctca      60
ctccgagccc aaatcttctg acaaaactca caca                                  94

<210> SEQ ID NO 2
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 2
cggagacaag cttaggctct tctgcgtgta gtggttgtgc ag                         42

<210> SEQ ID NO 3
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 3

Glu Pro Lys Ser Cys Asp Lys Thr His Thr Cys Pro Pro Cys Pro
1               5                   10                  15

<210> SEQ ID NO 4
<211> LENGTH: 68
<212> TYPE: DNA
<213> ORGANISM: Artificial Sequence
<220> FEATURE:
<223> OTHER INFORMATION: Synthetic Polynucleotide

<400> SEQUENCE: 4
gcctaagctt gtctccgggt gcctgacatc accatcacca tcactaagcc ccagtgtgga      60
tgctgttg                                                              68

<210> SEQ ID NO 5
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 5
agaagctcca agaactgctg gcag                                             24
```

<210> SEQ ID NO 6
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 6
cctgccagca gttcttggag cttct                                    25

<210> SEQ ID NO 7
<211> LENGTH: 33
<212> TYPE: DNA
<213> ORGANISM: Artificial Sequence
<220> FEATURE:
<223> OTHER INFORMATION: Synthetic Polynucleotide

<400> SEQUENCE: 7
agctctcgag gccaaatgag atgaggacgt gag                           33

<210> SEQ ID NO 8
<211> LENGTH: 68
<212> TYPE: DNA
<213> ORGANISM: Artificial Sequence
<220> FEATURE:
<223> OTHER INFORMATION: Synthetic Polynucleotide

<400> SEQUENCE: 8
gcctaagctt gtctccgggt gcctgccatc accatcacca tcactaagcc ccagtgtgga    60
tgctgttg                                                       68

<210> SEQ ID NO 9
<211> LENGTH: 71
<212> TYPE: DNA
<213> ORGANISM: Artificial Sequence
<220> FEATURE:
<223> OTHER INFORMATION: Synthetic Polynucleotide

<400> SEQUENCE: 9
gcctaagctt gtctccgggt gcctgacggc atcaccatca ccatcactaa gccccagtgt    60
ggatgctgtt g                                                   71

<210> SEQ ID NO 10
<211> LENGTH: 31
<212> TYPE: DNA
<213> ORGANISM: Artificial Sequence
<220> FEATURE:
<223> OTHER INFORMATION: Synthetic Polynucleotide

<400> SEQUENCE: 10
aggagcagta cgccagcacg taccgtgtgg t                             31

<210> SEQ ID NO 11
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 11
gtggtttgtc caaactcatc                                          20

<210> SEQ ID NO 12
<211> LENGTH: 31

```
<212> TYPE: DNA
<213> ORGANISM: Artificial Sequence
<220> FEATURE:
<223> OTHER INFORMATION: Synthetic Polynucleotide

<400> SEQUENCE: 12
accacacggt acgtgctggc gtactgctcc t                                31

<210> SEQ ID NO 13
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 13
agcagagctc gtttagtgaa ccg                                         23

<210> SEQ ID NO 14
<211> LENGTH: 57
<212> TYPE: DNA
<213> ORGANISM: Artificial Sequence
<220> FEATURE:
<223> OTHER INFORMATION: Synthetic Polynucleotide

<400> SEQUENCE: 14
ccaagggccc atcggtcttc ccctggcac cctcctccaa gagcacctct gggggca      57

<210> SEQ ID NO 15
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 15
atgtcatgtg tgagttttgt cacaagattt gggctcaact ttctt                 45

<210> SEQ ID NO 16
<211> LENGTH: 69
<212> TYPE: DNA
<213> ORGANISM: Artificial Sequence
<220> FEATURE:
<223> OTHER INFORMATION: Synthetic Polynucleotide

<400> SEQUENCE: 16
tcttgtgaca aaactcacac atgacatcac catcaccatc actaagcccc agtgtggatg  60
ctgttgcca                                                         69

<210> SEQ ID NO 17
<211> LENGTH: 40
<212> TYPE: DNA
<213> ORGANISM: Artificial Sequence
<220> FEATURE:
<223> OTHER INFORMATION: Synthetic Polynucleotide

<400> SEQUENCE: 17
ctaggtcgac tttatttgcc aaatgagatg aggacgtgag                       40

<210> SEQ ID NO 18
<211> LENGTH: 9
<212> TYPE: PRT
<213> ORGANISM: Artificial Sequence
<220> FEATURE:
<223> OTHER INFORMATION: Synthetic Polypeptide
```

```
<400> SEQUENCE: 18

Lys Ser Leu Ser Leu Ser Pro Gly Lys
1               5

<210> SEQ ID NO 19
<211> LENGTH: 50
<212> TYPE: DNA
<213> ORGANISM: Artificial Sequence
<220> FEATURE:
<223> OTHER INFORMATION: Synthetic Polynucleotide

<400> SEQUENCE: 19
gcctaagctt gtctccgggt gcctgataag ccccagtgtg gatgctgttg             50

<210> SEQ ID NO 20
<211> LENGTH: 33
<212> TYPE: DNA
<213> ORGANISM: Artificial Sequence
<220> FEATURE:
<223> OTHER INFORMATION: Synthetic Polynucleotide

<400> SEQUENCE: 20
agctctcgag gccaaatgag atgaggacgt gag                               33
```